US010222304B2

(12) United States Patent
Dave et al.

(10) Patent No.: US 10,222,304 B2
(45) Date of Patent: Mar. 5, 2019

(54) DEPOSITION AND IMAGING OF PARTICLES ON PLANAR SUBSTRATES

(71) Applicant: Massachusetts Institute of Technology, Cambridge, MA (US)

(72) Inventors: Shivang R. Dave, Boston, MA (US); German Gonzalez Serrano, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 526 days.

(21) Appl. No.: 14/774,569

(22) PCT Filed: Mar. 14, 2014

(86) PCT No.: PCT/US2014/028193
§ 371 (c)(1),
(2) Date: Sep. 10, 2015

(87) PCT Pub. No.: WO2014/143981
PCT Pub. Date: Sep. 18, 2014

(65) Prior Publication Data
US 2016/0076978 A1 Mar. 17, 2016

Related U.S. Application Data

(60) Provisional application No. 61/793,295, filed on Mar. 15, 2013.

(51) Int. Cl.
*G01N 1/28* (2006.01)
*B01J 19/00* (2006.01)

(52) U.S. Cl.
CPC ........ *G01N 1/2813* (2013.01); *B01J 19/0046* (2013.01); *B01J 2219/0036* (2013.01);
(Continued)

(58) Field of Classification Search
None
See application file for complete search history.

(56) References Cited

U.S. PATENT DOCUMENTS 4,089,989 A 5/1978 White et al.
4,209,548 A 6/1980 Bacus
(Continued)

FOREIGN PATENT DOCUMENTS

EP 0 955 084 A1 11/1999
WO WO 95/25116 A1 9/1995
(Continued)

OTHER PUBLICATIONS

Allan et al., "Detection and Quantification of Circulating Tumor Cells in Mouse Models of Human Breast Cancer Using Immunomagnetic Enrichment and Multiparameter Flow Cytometry," *Cytom. Part A*, 65A(1):4-14 (2005).
(Continued)

*Primary Examiner* — Erik B Crawford
(74) *Attorney, Agent, or Firm* — Hamilton, Brook, Smith & Reynolds, P.C.

(57) ABSTRACT

Among other aspects, the present invention provides for the deposition of biological particles, such as cells, in a liquid, in a desired two-dimensional pattern on a planar surface of a substrate so as to permit rapid, simple, and sensitive detection of cells and/or sub-cellular components (e.g., proteins, biomarkers) disposed on the substrate. In various aspects, the systems and methods can enable reproducible high-throughput screening and/or allow for sensitive and specific detection of rare events in heterogeneous cell populations within a biological sample, with limited or no selective cell loss or sample enrichment.

12 Claims, 16 Drawing Sheets

(52) U.S. Cl.
CPC ............. *B01J 2219/00527* (2013.01); *B01J 2219/00691* (2013.01); *B01J 2219/00743* (2013.01)

(56) References Cited

U.S. PATENT DOCUMENTS

| | | | |
|---|---|---|---|
| 4,252,538 | A | 2/1981 | Barr |
| 5,508,200 | A | 4/1996 | Tiffany et al. |
| 6,395,562 | B1 * | 5/2002 | Hammock ............ G01N 33/543 204/406 |
| 6,479,052 | B1 | 11/2002 | Marshall et al. |
| 6,518,056 | B2 * | 2/2003 | Schembri ............ B01J 19/0046 435/287.2 |
| 6,594,432 | B2 * | 7/2003 | Chen .................... B01J 19/0046 385/127 |
| 7,051,654 | B2 * | 5/2006 | Boland ................. B01L 3/0268 101/483 |
| 7,384,793 | B2 | 6/2008 | McCash et al. |
| 8,119,391 | B2 * | 2/2012 | Kim ...................... B01L 3/0244 435/283.1 |
| 8,248,597 | B2 | 8/2012 | Goldberg |
| 8,921,040 | B2 * | 12/2014 | Corbett ............ G01N 35/00029 435/6.1 |
| 2004/0161804 | A1 | 8/2004 | McCash et al. |
| 2006/0248944 | A1 | 11/2006 | Gleich et al. |
| 2009/0181863 | A1 * | 7/2009 | Milstein ................ G01N 33/68 506/18 |
| 2009/0208577 | A1 * | 8/2009 | Xu ......................... A61L 27/38 424/484 |
| 2009/0317836 | A1 | 12/2009 | Kuhn et al. |
| 2010/0247492 | A1 | 9/2010 | Kuhn et al. |
| 2012/0115179 | A1 | 5/2012 | Hauden et al. |
| 2012/0148742 | A1 | 6/2012 | Kelekar |

FOREIGN PATENT DOCUMENTS

| | | |
|---|---|---|
| WO | 2002084266 A2 | 10/2002 |
| WO | 2006133392 A1 | 12/2006 |
| WO | WO 2007/089911 | 8/2007 |
| WO | WO 2010/028160 | 3/2010 |
| WO | WO 2011/028905 | 3/2011 |
| WO | WO 2011/050103 | 4/2011 |

OTHER PUBLICATIONS

Alunni-Fabbroni et al., "Circulating Tumour Cells in Clinical Practice: Methods of Detection and Possible Characterization," *Methods*, 50(4):289-297 (2010).
Ben Hsieh et al., "High Speed Detection of Circulating Tumor Cells," *Biosens. Bioelectron.*, 21(10):1893-1899 (2006).
Berezhna, "Fast Multi-Spectral Imaging Technique for Detection of Circulating Endothelial Cells in Human Blood Samples Fast Multi-Spectral Imaging Technique for Detection of Circulating Endothelial Cells in Human Blood Samples (2012)."
Cho et al., "Characterization of Circulating Tumor Cell Aggregates Identified in Patients With Epithelial Tumors," vol. 016001 (2012).
Cui et al., "Lensless High-Resolution On-Chip Optofluidic Microscopes for Caenorhabditis Elegans and Cell Imaging," *Proc. Natl. Acad. Sci.*, 105(31):10670-10675 (2008).
Gerges et al., "New Technologies for the Detection of Circulating Tumour Cells," pp. 49-64 (2010).
Goda et al., "High-Throughput Single-Microparticle Imaging Flow Analyzer," *Proc. Natl. Acad. Sci.*, 109(29):11630-11635 (2012).
Hosokawa et al., "Size-Selective Microcavity Array for Rapid and Efficient Detection of Circulating Tumor Cells," 82(15):6629-6635 (2010).
Issadore et al., "Ultrasensitive Clinical Enumeration of Rare Cells ex Vivo Using a Micro-Hall Detector," 4(141) (2012).
Kraeft et al., "Reliable and Sensitive Identification of Occult Tumor Cells Using the Improved Rare Event Imaging System," 10(617):3020-3028 (2004).
Krivacic et al., "A Rare-Cell Detector for Cancer," *Proc. Natl. Acad. Sci. U. S. A.*, 101(29):10501-10504 (2004).
Lazar et al., "Cytometric Comparisons Between Circulating Tumor Cells From Prostate Cancer Patients and the Prostate-Tumor-Derived LNCaP Cell Line," *Phys Biol.*, 9(1):016002 (2012).
Li et al., "An Immunomagnetic Single-Platform Image Cytometer for Cell Enumeration Based on Antibody Specificity," *Clin. Vaccine Immunol.*, 14(4):412-419 (2007).
Lin et al., "Portable Filter-Based Microdevice for Detection and Characterization of Circulating Tumor Cells," *Clin. Cancer Res.*, 16(20):5011-5018 (2010).
Marrinucci et al., "Fluid Biopsy in Patients With Metastatic Prostate, Pancreatic and Breast Cancers," *Phys Biol.*, 9(1):016003 (2012).
Mckenna et al., "384-Channel Parallel Microfluidic Cytometer for Rare-Cell Screening," pp. 305-310 (2009).
Nagrath et al., "Isolation of Rare Circulating Tumour Cells in Cancer Patients by Microchip Technology," *Nature*, 450(7173):1235-1239 (2007).
Nieva et al., "High-Definition Imaging of Circulating Tumor Cells and Associated Cellular Events in Non-Small Cell Lung Cancer Patients: A Longitudinal Analysis," *Phys Biol.*, 9(1):016004 (2012).
Rodriguez et al., "A Microchip CD4 Counting Method for HIV Monitoring in Resource-Poor Settings," *PLoS Med.*, 2(7):e182 (2005).
Schiro et al., "Sensitive and High-Throughput Isolation of Rare Cells from Peripheral Blood with Ensemble-Decision Aliquot Ranking **," *Angew Chem Int Ed Engl.*, 51(19):4618-4622 (2012).
Shapiro et al., "Cellular Astronomy—A Foreseeable Future in Cytometry," *Cytometry*, 60A(2):115-124 (2004).
Simonnet et al., "High-Throughput and High-Resolution Flow Cytometry in Molded Microfluidic Devices," *Anal. Chem.*, 78(16):5653-5663 (2006).
Stott et al., "Isolation and Characterization of Circulating Tumor Cells from Patients with Localized and Metastatic Prostate Cancer," *Sci. Transl. Med.*, 2(25):25ra23-25ra23 (2010).
Wendel et al., "Fluid Biopsy for Circulating Tumor Cell Identification in Patients With Early-And Late-Stage Non-Small Cell Lung Cancer: A Glimpse Into Lung Cancer Biology," *Phys Biol.*, 9(1):016005 (2012).
Xue et al., "Isolation and Elution of Hep3B Circulating Tumor Cells Using a Dual-Functional Herringbone Chip," pp. 605-612 (2014).
Notification of Transmittal of the International Search Report and the Written Opinion of the International Searching Authority, International Application No. PCT/US2014/028193, dated Jul. 14, 2014, entitled "Deposition and Imaging of Particles on Planar Substrates".
Arumuganathar et al., "Aerodynamically Assisted Bio-Jets: The Development of a Novel and Direct Non-Electric Field-Driven Methodology for Engineering Living Organisms", Biomed. Mater. 2:158-168, May 17, 2007.
Assadi et al., "Bonding Mechanism in Cold Gas Spraying", Acta Materialia, 51:4379-4394, May 5, 2003.
"An Australian "blood artist" has painted a portrait of Marilyn Manson using an airbrush connected directly into his bloodstream via an intravenous tube.", Mar. 12, 2012, downloaded from www.news.ninemsn.com.au on Feb. 26, 2013.
I Van der Auwera et al., "Circulating Tumour Cell Detection: A Direct Comparison Between the CellSearch System, The AdnaTest and CK-19/Mammaglobin RT-PCR in Patients with Metastatic Breast Cancer", British Journal of Cancer 102(2):276-284, Jan. 19, 2010.
Choonee et al., "Post Processing of Microstructures by PDMS Spray Deposition", Sensors and Actuators A Physical, 155(2):253-262, Oct. 2009.
Gupta et al., "Identification of Selective Inhibitors of Cancer Stem Cells by High-Throughput Screening", Cell, 138 (645-659), Aug. 21, 2009.
Huang et al., "A Microfluidics Approach for the Isolation of Nucleated Red Blood Cells (NRBCs) from the Peripheral Blood of Pregnant Woman", Prenatal Diagnosis, 28:892-899, Oct. 2008.
Issadore et al., "Ultrasensitive Clinical Enumeration of Rare Cells ex Vivo Using a Micro-Hall Detector", Science Translational Medicine, 4(141):141ra92:1-10, Jul. 4, 2012.

(56) References Cited

OTHER PUBLICATIONS

Jayasinghe et al., "Electric Field Driven Jetting: An Emerging Approach for Processing Living Cells", Biotechnology Journal, 1:86-94, Jan. 2006.

Joly et al., "Bio-Electrospraying and Aerodynamically Assisted Bio-Jetting Whole Human Blood: Interrogating Cell Surface Marker Integrity", Biomicrofluidics, 4(1):11101, Jan. 13, 2010.

Jocelyn Kaiser, "Cancer's Circulation Problem", Science, vol. 327, Feb. 27, 2010.

Komyei et al., "Cell Sorting in a Petri Dish Controlled by Computer Vision", Scientific Reports, 3:1088, (11 pages) Jan. 18, 2013.

Lin et al., "Disseminated and Circulating Tumor Cells: Role in Effective Cancer Management", Critical Reviews in Oncology/Hematology, 77(1):1-11, Jan. 2011.

McLeod et al., "Toward Giga-Pixel Nanoscopy on a Chip: a Computational Wide-Field Look at the Nano-Scale without the Use of Lenses", Lab Chip, 13(11):2028-2035, Jun. 7, 2013.

Mudanyali et al., "Wide-field optical detection of nanoparticles using on-chip microscopy and self assembled nanolenses," Nature Photonics, vol. 7, pp. 247-254, Mar. 2013.

Shapiro et al., "Personal Cytometers: Slow Flow of No Flow?" International Society for Analytical Cytology, pp. 620-630, 2006.

Singh et al., "EMT, cancer stem cells and drug resistance: an emerging axis of evil in the war on cancer," Ocogene, vol. 29, pp. 4741-4751, 2010.

Wittrup et al., "Fluarescence Array Detector for Large-Field Quantitative Fluorescence Cytometry," Cytometry, vol. 16, pp. 2016-2213, 1994.

Yamamura et al., "Single-Cell Microarray for Analyzing Cellular Response," Analytical Chemistry, vol. 77, No. 24, pp. 8050-8056, Dec. 15, 2005.

Yoshimoto et al., "An automated system for high-throughput single cell-based breeding," Scientific Reports, 9 pages, Feb. 1, 2013.

Zhao et al., "Optofluidic imaging: now and beyond," The Royal Society of Chemistry, Lab Chip, vol. 13, pp. 17-24, 2013.

Zhu et al., "Optical imaging techniques for point-of-care diagnostics," The Royal Society of Chemistry, Lab Chip, vol. 13, pp. 51-67, 2013.

\* cited by examiner

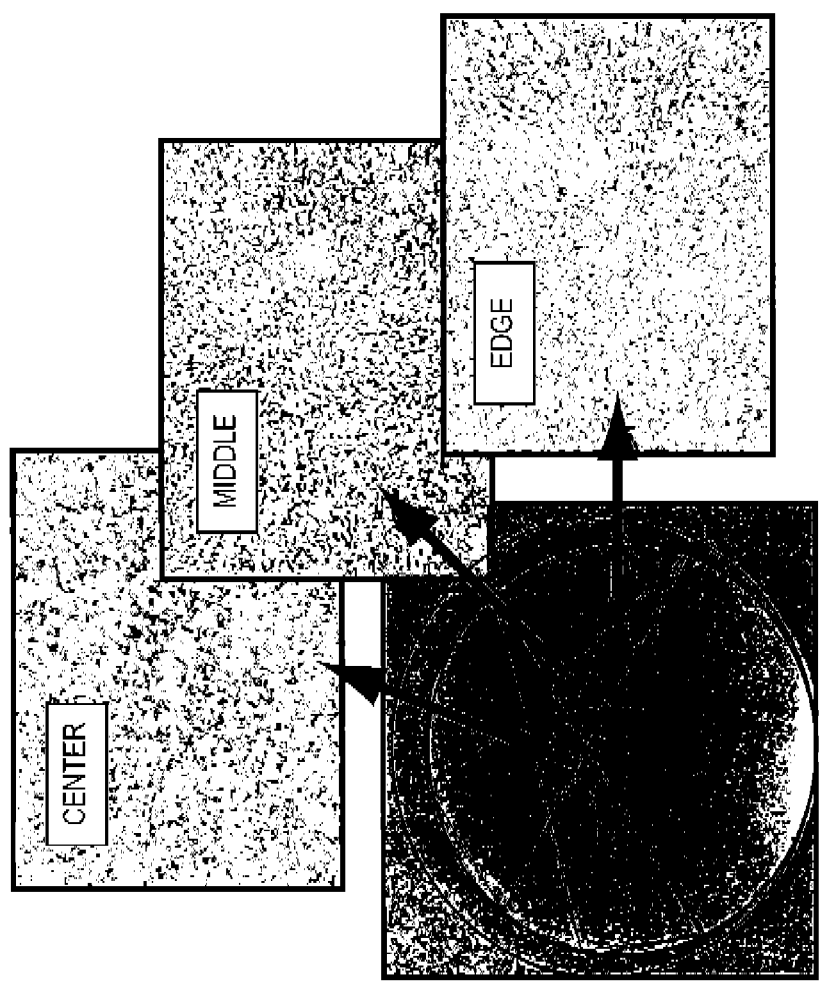

DEPOSITION AND IMAGING OF PARTICLES ON PLANAR SUBSTRATES

RELATED APPLICATION

This application is the U.S. National Stage of International Application No. PCT/US2014/028193, filed Mar. 14, 2014 which designates the U.S., is published in English, and claims the benefit of U.S. Provisional Application No. 61/793,295, filed Mar. 15, 2013. The entire teachings of that application are incorporated herein by reference.

BACKGROUND OF THE INVENTION

In many fields, the efficient detection and quantification of particles depends on the ability first to deposit those particles on a planar substrate. Consider, for example, the challenge of detecting and quantifying the contents of a drop of whole blood under a microscope. Whole blood contains various types of particles (e.g., different kinds of blood cells) suspended in serum. If a drop of blood were viewed under a microscope without first making an effort to spread the blood cells apart from each other, the blood cells would appear as overlapping images under the microscope, making them difficult to count, identify, or study individually. Accordingly, it is important to separate the blood cells from each other before studying them, such as by distributing them across the surface of a planar substrate, e.g., a glass microscope slide. In some fields, the efficient detection and quantification of particles further depends on the ability to deposit the particles on the substrate in a desired arrangement, e.g., in a two-dimensional pattern, to a uniform height, in a monolayer, in relatively close proximity to one other, or some combination of the foregoing.

One field that depends on the ability first to deposit particles on planar substrates before analyzing the particles is "cellular astronomy." Cellular astronomy is known and described in the art. See, e.g., Howard M. Shapiro, *Cellular Astronomy—A Foreseeable Future in Cytometry*, 60A CYTOMETRY PART A 115-124 (2004). Briefly, and in one aspect, cellular astronomy can achieve the systematic examination of very large numbers of cells by first spreading the cells over the surfaces of one or more substrates, and by then using imaging technology to systematically examine the cells. Typically, an imager starts by simultaneously examining cells visible within a field of view, and continues by moving the field of view across the substrate, continuing region by region until the desired portion of the substrate has been imaged.

One important application of cellular astronomy is the detection and quantification of cell types present in a mixture of cells. For example, in the treatment and management of cancer, it is useful to know whether circulating tumor cells ("CTCs") are present among other cells in the blood. Because CTCs are known to occur in very low concentrations, for example 1 CTC per 1,000,000,000 blood cells, it is necessary to inspect a very large number of cells in order to determine with confidence whether or not CTCs are present. In order to ensure that cells are examined and accurately identified, it is desirable that they be spread in a monolayer. In order to decrease the number of regions that must be studied and thereby speed the process, it is further desirable that cells be spaced relatively closely together.

Although many technologies, such as cellular astronomy, rely on the ability to deposit particles on planar substrates in a desired two-dimensional pattern, existing methods for depositing particles on substrates are limited in their scope, utility, or versatility. Accordingly, there exists a need for new and improved methods and systems for quickly and efficiently depositing particles, such as cells, onto a flat surface in a desired arrangement, allowing the particles to be studied.

SUMMARY OF THE INVENTION

The present invention is related to the discovery of new, improved, and versatile methods and apparatus for quickly and efficiently depositing particles, such as cells, onto substrates in a desired arrangement, and optionally inspecting them.

In one embodiment, the invention relates to an apparatus for dispensing particles in a liquid medium onto a substrate in a desired two-dimensional pattern. The apparatus includes a dispenser having an aperture that directs the particles toward a movable target zone on the substrate. The trajectory of the movable target zone is controlled by controlling the location or orientation of the dispenser aperture, the substrate, or both.

In another embodiment, the invention relates to an apparatus for particle analysis. The apparatus includes a dispenser having an aperture that directs the particles toward a movable target zone on the substrate so as to produce a two-dimensional pattern, and a controller for moving the movable target zone along a desired trajectory while the dispenser is dispensing particles. In addition, the apparatus has an inspection system for analyzing particles deposited in the movable target zone.

In a preferred embodiment, the invention relates to an apparatus for dispensing particles in a liquid medium onto a substrate, wherein the apparatus has a dispenser with an aperture, a substrate that rotates about a central, perpendicular axis, and a rotator that rotates the substrate about the axis while particles are being dispensed.

In yet another embodiment, the invention relates to a method for dispensing particles in a liquid medium onto a substrate in a desired two-dimensional pattern, wherein the particles are introduced into a particle dispenser, dispensed through the aperture of a dispenser, and deposited on a movable target zone on the substantially planar surface of the substrate. The center of the movable target zone is guided along a path on the substantially planar surface while the dispenser is dispensing particles.

In still another embodiment, the invention relates to a method for inspecting particles disposed within a liquid solution. The particle-containing solution is introduced into the dispenser and then dispensed through an aperture toward a movable target zone on a planar surface of the substrate. The center of the target zone is guided along a desired path on the surface while particles are being dispensed, resulting in a two-dimensional pattern of particles on the surface. A portion of the particles are then inspected.

In another preferred embodiment, the invention relates to a method for detecting one or more cells from a population of cells in a liquid, wherein spin-brushing is used to deposit the population of cells in the liquid onto a planar surface so as to achieve a monolayer of cells over at least a portion of the surface, and cellular astronomy is used to image at least a portion of the cellular monolayer.

Embodiments of the present invention can permit rapid, simple, and sensitive detection of particles, such as cells and/or sub-cellular components (e.g., proteins, nucleic acids, sub-cellular complexes). Where the particles are cells or other biological particles, embodiments of the invention can aid in the identification, quantification, diagnosis of a disease state, prediction of disease progress, and/or prognostication of therapeutic outcome. In various aspects, the systems and methods of the invention can enable analysis and quantification of cells of a wide variety of abundance, reproducible high-throughput screening, and/or allow for sensitive and specific detection of rare events in heterogeneous cell populations within a biological sample, with limited or no selective cell loss or sample enrichment.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 6 depicts an exemplary distribution of cells dispensed onto a substrate in accordance with aspects of the present invention.

DETAILED DESCRIPTION OF THE INVENTION

Definitions

Figure 1:
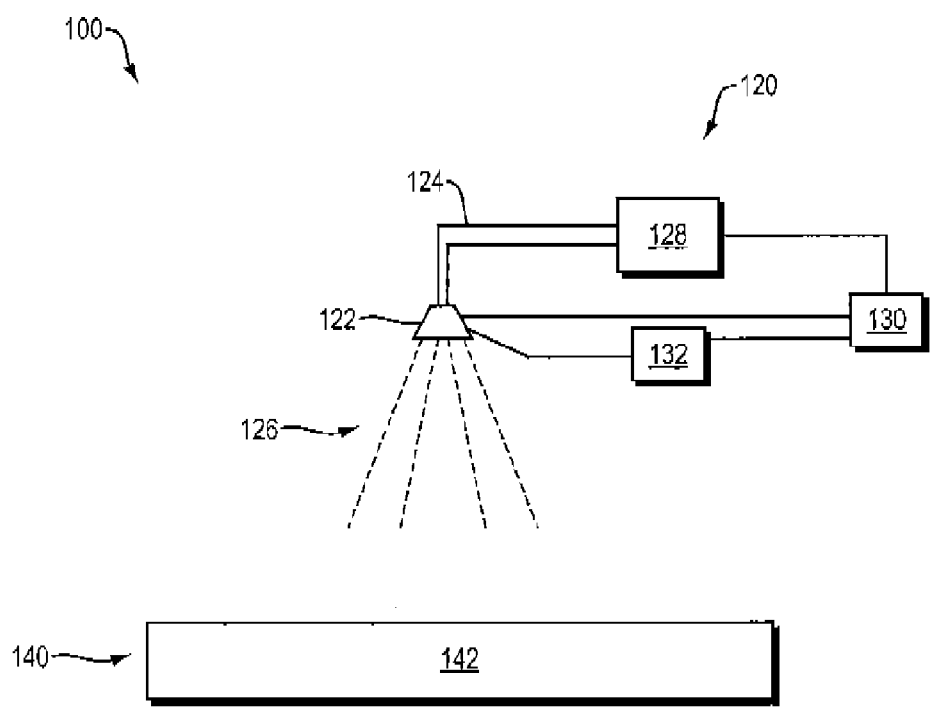
FIG. 1 is a schematic representation of an apparatus for dispensing particles contained in a liquid onto a planar substrate, according to this invention.

Unless otherwise defined, all technical and scientific terms used herein have the same meaning as commonly understood by one of ordinary skill in the art to which this invention pertains.

"Biological material," as used herein, refers to a product of a living organism. In some embodiments, biological materials are (a) biological fluids, e.g., blood, urine, cerebrospinal fluid, interstitial fluid, sperm, amniotic fluid, ascites, bronchial lavage, effluent pleural fluid, joint fluid, saliva, pericardial fluid, cervical fluid, and mucous; (b) components of products of living organisms, e.g., cellular and sub-cellular particles; (c) cells, e.g., human cells, eukaryotic cells, prokaryotic cells, primate cells, blood cells, red blood cells, white blood cells, tumor cells, circulating tumor cells, cervical cells (Pap smear) and platelets; (d) portions or products of cells, e.g., sub-cellular particles, proteins and nucleic acids; (e) biomarkers; and (f) materials from clinical tests or procedures, e.g., anal smear, cervical smear, and buccal smear. Some biological samples can contain added non-biological materials, such as polymers, surfactants, salts, biomolecules, or other reagents useful in cell processing.

"Particle," as used herein, refers to a discrete quantity of matter having a wide range of sizes. For example, particles can have a median particle size in the range of from about 3 nm to about 3 mm. A preferred range of particle size is from about 10 nm to 1 mm. Another preferred range of particle size is from about 0.5 um to 100 um. Yet another preferred range of particle size is from about 50 nm to 5 um. Particles are not limited to a particular shape or composition. There are a wide range of techniques that can be utilized to characterize the particle size of a material. Those skilled in the art also understand that almost all these techniques do not physically measure the actual particle size, but measure one or more physical phenomena which are interpreted to indicate a particle size. As part of the interpretation process some assumptions need to be made to enable mathematical calculations to be made. These assumptions deliver results such as an equivalent spherical particle size, or a hydrodynamic radius. Amongst these various methods, two types of measurements are most commonly used. Photon correlation spectroscopy (PCS), also known as 'dynamic light scattering' (DLS) is commonly used to measure particles with a size less than 10 micron. Typically this measurement yields an equivalent hydrodynamic radius often expressed as the average size of a number distribution. The other common particle size measurement involves laser diffraction which is commonly used to measure particle size from 100 nm to 2000 micron. This technique calculates a volume distribution of equivalent spherical particles that can be expressed using descriptors such as the median particle size or the % of particles under a given size. Those skilled in the art recognize that different characterization techniques such as photon correlation spectroscopy and laser diffraction measure different properties of a particle ensemble. As a result multiple techniques will give multiple answers. For measurements made using a photon correlation spectroscopy instrument, or an equivalent method known in the art, the term "number average particle size" is defined as the average particle diameter as determined on a number basis. For measurements made using a laser diffraction instrument, or an equivalent method known in the art, the term "median particle size" is defined as the median particle diameter as determined on an equivalent spherical particle volume basis. Where the term median is used, it is understood to describe the particle size that divides the population in half such that 50% of the population is greater than or less than this size. Those skilled in the art will recognize which one of these various techniques of measuring particle size, or other method, is best suited to determining the average particle size or median particle size for particles such as nanobeads, cells, subcellular particles, etc.

"Biological particle," as used herein, refers to particles that are biological materials, as well as to non-biological particles that bind to, attach to, or encapsulate a biological material.

"Cellular astronomy," as used herein, refers to the field described in Howard M. Shapiro, *Cellular Astronomy—A Foreseeable Future in Cytometry,* 60A CYTOMETRY PART A 115-124 (2004).

"Biological capture bead," as used herein, refers to any bead that has the intrinsic property of, or has been modified by conjugation, functionalization, or other means to have the property of, binding to a biological material. Biological capture beads can have, without limitation, surface-exposed proteins, carbohydrates, antibodies, nucleic acids, antigens, biomarkers, antibodies, aptamers, or other features for which a biological material has affinity.

"Spin-brushing," as used herein, refers to the application of a material onto a surface of a rotating substrate by dispensing it through a spraybrush-type dispenser, such as, for example, an airbrush.

Example Embodiments

A description of example embodiments of the invention follows. The following detailed description should be read with reference to the drawings. The drawings, which are not necessarily to scale, depict selected embodiments and are not intended to limit the scope of the invention. The detailed description illustrates by way of example, and is not intended to limit the scope of the invention. It will be apparent that the described embodiments are susceptible to alteration or variation according to common general knowledge without departing from the scope of the disclosure.

As illustrated in FIG. 1, an apparatus 100 for dispensing particles includes a dispenser 120 for dispensing particles in a liquid medium and a substrate 140 having a planar surface 142 upon which the dispensed particles are deposited. Planar surface 142 is disposed in a facing relationship to the dispenser 120. The dispenser terminates in an aperture such as nozzle 122, through which particles pass and are directed toward the substrate. A wide variety of apertures can be used, and depending on the dispenser, the aperture can play a relatively active or a passive role in the dispensing and/or directing process. The nozzle 122 of dispenser 120 is separated from the surface 142 by a gap, which is typically filled with a gaseous medium such as air or inert gas. In some embodiments the gap can be maintained at a reduced pressure relative to the atmosphere and possibly at, or at a near vacuum.

Various commercially available polystyrene Petri dishes can, in some embodiments, serve as an exemplary substrate. However, substrate 140 can be composed of a wide variety of materials. These materials can include rigid materials such as glass, silicon, polystyrene, polycarbonate, and acrylic, as well as soft materials, such as Poly(dimethyl)siloxane (PDMS) and similar polymers, and fibrous materials such as paper. These materials also include both opaque materials as well as transparent materials, including optically transparent materials suitable for transmission microscopy therethrough. Suitable materials can have varying surface properties, including both hydrophobic and hydrophilic properties. Further, various portions of the substrate can be composed of different materials. For example, the planar surface of a hydrophilic substrate can be modified by coating it with a substantially hydrophobic material. This can help, in some cases, to promote in achieving a desired distribution of biological particles, e.g., cells, across the surface. Alternatively, a hydrophilic surface can, in appropriate instances, be utilized to better facilitate fluid spreading.

A wide variety of dispensers 120 can be used for dispensing particles in a liquid medium onto the planar surface of the substrate. In preferred embodiments the dispenser produces a spray, preferably by aerosolizing the liquid. Other techniques of generating sprays are well known in the art, e.g., electrospraying.

The dispenser directs droplets of the spray, which contain particles, to a target zone on the surface of the substrate. After a droplet lands on the substrate, the particles can remain dissolved in or suspended in the droplet for a period of time. After landing, the droplets can change shape or move along the surface of the substrate, depending, for example, on a variety of physical parameters, including the size of the droplet, the droplet's hydrophilicity relative to that of the surface, and forces acting on the deposited droplet. Forces on a droplet can include, for example, shear forces upon landing on a moving substrate and centrifugal forces following landing on a substrate that is rotating. Deposited droplets can also come into contact with each other, joining to produce larger droplets, or dispersing across the surface of the substrate as a film. Particles in the droplets or in the film can, according to their chemical and physical properties as well as those of both the liquid and the surface, come to be deposited on the surface. As particles settle toward the surface they can come into contact with each other, possibly interacting with each other. If these interactions are strong it can be desirable to lower the concentration of particles in the liquid medium, or make other adjustments, to decrease the chance of interactions between particles and to enhance the desired and timely deposition of the particles on the substrate in the desired pattern.

A wide variety of materials can be dispensed by dispenser 120. In one embodiment the material is a liquid that contains particles and preferably biological particles. The particles can be either dissolved in or suspended in the liquid. In a preferred embodiment, the material is whole blood, which contains a variety of cells. In other embodiments, the particles are not biological, such as fabricated nanoparticles, beads, styrene beads, agarose beads, magnetic beads, and inorganic particles. The particles can also be beads or nanoparticles to which proteins, nucleic acids, carbohydrates, antibodies, antigens, or other biomarkers have been conjugated or otherwise attached. It is also possible and within the scope of the invention to deposit beads that are complexed to other materials, including other particles, onto the substrate.

In a preferred embodiment, the bead is a biological capture bead. In various embodiments of the invention, beads, e.g., biological capture beads are deposited onto the planar surface of the substrate, and are then brought into contact, e.g., washed, with a solution or suspension comprising an analyte, such as a biological material, protein, a nucleic acid, or a lipid. In this manner there can be reaction between or combination of the analyte and bead, e.g., biological capture bead, on the substrate. The biological analyte then be interrogated, imaged, detected, analyzed, probed, or further reacted, as desired.

It is not essential to the invention that particles remain surrounded by liquid for the duration of the deposition process. Particles can become partially or fully desolvated while exiting, or after exiting, the aperture of the dispenser. For example, droplets can break apart in flight owing to various forces such as electrostatic repulsion forces, in the case of electrospraying, or aerodynamic drag forces. In addition, liquid can evaporate from the droplet or from the film, leaving partially or fully desolvated particles.

A wide variety of dispensers can be used as long as it can dispense the particles in a predetermined two-dimensional pattern. For example, the dispenser can comprise a nebulizer, atomizer, sonic agitator, electrosprayer, bioelectrosprayer, electrohydrodynamic atomizer, or employ any of various technologies known in the prior art, such as ink jet deposition and bio-electrojetting.

The system 100 can include a controller 130 for controlling the nozzle 122 of dispenser 120 and/or the pumps and valves 128 delivering the biological sample thereto so as to control, for example, the pressure and flow rate of the biological sample through the nozzle 122. The sample dispenser 120 can include one or more reservoirs, pumps, or valves 128 for storing and/or transporting the particle-containing liquid to the nozzle, or for facilitating a reaction of the sample in a desired fashion.

The dispenser can optionally have a variety of other features or properties. For example, the dispenser preferably is configured to produce a substantial dispersion of particles. For example, in a typical spray nozzle, a field of particle containing droplets will be emitted from the aperture. The field will have a general, or average direction, as well as a variance or dispersion around that general direction, which characterizes the spread of the spray. The greater the dispersion, the larger the target zone on the substrate will be, provided that the orientations of the aperture and substrate remain fixed. While any dispensing technology will emit particles from the aperture with some degree of dispersion, it is understood in the art that some dispensing methods are substantially dispersive, whereas others are relatively focused. For example, some technologies are known in the art that can guide particles or droplets to a tightly defined region, possibly through the use of laser beams or fine fibers for guidance. As it is a goal of the invention, in some aspects, to achieve a two-dimensional pattern of particles on a substrate, it is advantageous to use dispensers that are substantially dispersive, so as to provide coverage that is substantially two-dimensional, even in a single pass of the nozzle over the substrate. This is in contrast to what can be achieved with dispensers that are relatively focused, which would produce a line of deposited particles having insignificant width for purpose of this aspect of the invention. Further, to promote uniformity of distribution across the substrate, it is desirable that the dispenser produce a substantially random dispersion of particles.

The dispenser or another component of the apparatus can additionally be configured to be selective of the size or other characteristics, such as physical characteristics, of particles that it dispenses. For example, it can dispense various particles at rates that are disproportionate to their relative abundance in the particle-containing liquid that is being fed into the dispenser. This can result in the enrichment of the sample with respect to particles of interest. In some embodiments, a sample is selectively enriched in one or more components before being introduced into the dispenser.

Conversely, in other embodiments, the apparatus is not selective of the particles, and dispenses them substantially in the same ratio as their abundance in solution. This non-selectivity across a wide range of particle types and sizes can be desirable in fields such as Cellular Astronomy in which it can be important not to selectively bias the population of particles that are being presented to the substrate surface for inspection.

The dispenser can be adjustable in the flow rate with which it dispenses liquid from the aperture and in the average size of droplets that are emitted from the aperture and of droplets that reach the surface of the substrate. The volume of liquid reaching the substrate per unit time depends in part on both the size and number of droplets in the gap between the aperture and substrate. The faster that a dispenser emits droplets or particles, the greater the number of particles that will be present in the gap at a given time.

Preferably, the dispenser is configured to produce and maintain during operation a substantial multiplicity of droplets in the gap between the aperture and the substrate. Often, thin film formation can best be achieved by distributing a relatively large number of droplets of relatively small size over the substrate. In order to achieve the desired deposition in a relatively short period of time, it is desirable that the relatively large number of small droplets be emitted from the dispenser fairly quickly, with the result that it is desirable to have a substantial multiplicity of droplets in flight across the gap, at any one time. Spraying dispensers, such as aerosol-type dispensers are well-suited to producing such a substantial multiplicity of droplets. In contrast, some dispensing technologies tend to be configured to produce droplets that are relatively too large to be useful, or are produced too slowly to achieve substrate coverage in a desirable period of time. Accordingly, a dispenser capable of maintaining, during operation, a substantial multiplicity of droplets in the gap is preferred. Further preferred is a dispenser that is additionally capable of producing a relatively disperse distribution of droplets.

The dispenser can be configured to produce droplets, such as by aerosolization, either immediately before emission through the aperture or at some time or distance beforehand. In some embodiments, the preparation of a suitable gaseous suspension of particle-containing droplets can be achieved in a preliminary step or in a preliminary compartment or antechamber, and the suspension is then delivered to the dispenser.

By way of example, the sample dispenser 120 can transport a biological material to be dispensed through one or more conduits 124 to a nozzle 122 configured to generate a spray 126 containing a random dispersion of droplets (e.g., micro-droplets) of the biological sample. The random dispersion of the biological sample in the spray 126 and the controlled movement of the nozzle 122 and substrate 140 can be effective to generate a substantially uniform distribution of the biological material on the surface 142. In a preferred embodiment, the dispenser is preferably configured to dispense biological particles, e.g., blood cells, on the surface of the substrate so as to form a substantially uniform layer, preferably a monolayer. This uniformity can allow for one or more post-deposition processes (e.g., labeling, imaging, etc.), as discussed otherwise herein. The dispenser is further preferably configured to achieve a monolayer. The dispenser is also preferably configured to achieve a packing density of at least about 10%, preferably at least about 50%, and more preferably about 70% or more. This arrangement of particles on the surface 142 facilitates the rapid and sensitive downstream processing and/or analysis. In various aspects, the apparatus 100 can dispense a cell solution or suspension on the surface 142 of the substrate 140 and form a substantially uniform layer on the substrate so as to enable rapid, simple, and sensitive detection of cells and/or sub-cellular components (e.g., proteins, nucleic acids, sub-cellular complexes), with limited or no selective cell loss or sample enrichment prior to deposition on the surface of the substrate 140. As will be discussed in detail below, various post-deposition processing steps can additionally be performed to analyze a biological sample disposed on the substrate in accordance with the teachings herein.

The arrangement of particles on the surface of the substrate can be controlled by the system in a variety of ways. For example, the fluid dispersion rate, fluid dispersion location, fluid dispersion pressure, and relative motion of the substrate and particle dispenser can be controlled so as to deposit a particle monolayer having a desired packing density. In various embodiments, the monolayer can comprise at least about $10^6$ cells disposed on the surface. By way of another example, the cellular monolayer can comprise at least about $10^9$ cells disposed on the surface.

By way of example, the controller 130 can decrease the average spacing between cells, sub-cellular particles, or non-biological particles disposed on the surface 142 by increasing the speed of relative movement between the nozzle 122 and substrate 140 while maintaining a constant flow rate through the nozzle 122, further assuming that there is only one pass of the nozzle over the substrate. Additionally or alternatively, the controller 130 can control the average spacing between particles disposed on the surface 142 by altering the pressure and/or flow rate of the sample dispersed by the nozzle 122, or by making several passes of the nozzle over the same area.

More specifically, the arrangement of the particles on the surface of the substrate can be controlled in some aspects of the invention by translational or rotational movement of the substrate, the aperture (e.g., nozzle) of the dispenser, or both. With reference still to FIG. 1, it will be appreciated that the substrate 140 and the nozzle 122 can be configured to move relative to one another such that the spray 126 generated by the nozzle 122 can be sequentially directed to various portions of the surface 142 of the substrate 140. By way of example, the controller 130 can direct a scanner 132 to translate the nozzle 122 in the x-y plane relative to the surface 142. Various motions of the nozzle 122 in the x-y plane are possible. By way of non-limiting examples, the nozzle 122 can move in the x-y plane in a grid pattern, in straight lines, in a circle or in a spiral. Moreover, although the above description indicates that the nozzle 122 moves over a stationary substrate 140, it should be understood that it is the relative movement that results in the distribution of the sample on the substrate 140, as discussed in detail below. As such, it should be appreciated that a scanner could alternatively be coupled to the substrate 140 such that the nozzle 122 remains stationary while the substrate 140 moves relative thereto, again moving the nozzle relative to the substrate, such as in the x-y plane, and such as in a grid pattern, in straight lines, in a circle or in a spiral. Likewise, both the nozzle 122 and substrate 140 can be moved by one or more scanners to produce the relative movement. The one or more scanners can be connected to one or more controllers that control and coordinate their motions to produce the desired displacement of the nozzle relative to the substrate. Alternatively, the nozzle 122 can be fixed in the x-y plane but configured to pivot and thereby dispense the sample along different angular directions toward the substrate surface 142. In one aspect, the substrate can be configured to rotate as the cell dispenser dispenses the biological fluid. Finally, the dispenser can be configured to pass over a given area of the substrate more than once.

Figure 2A:
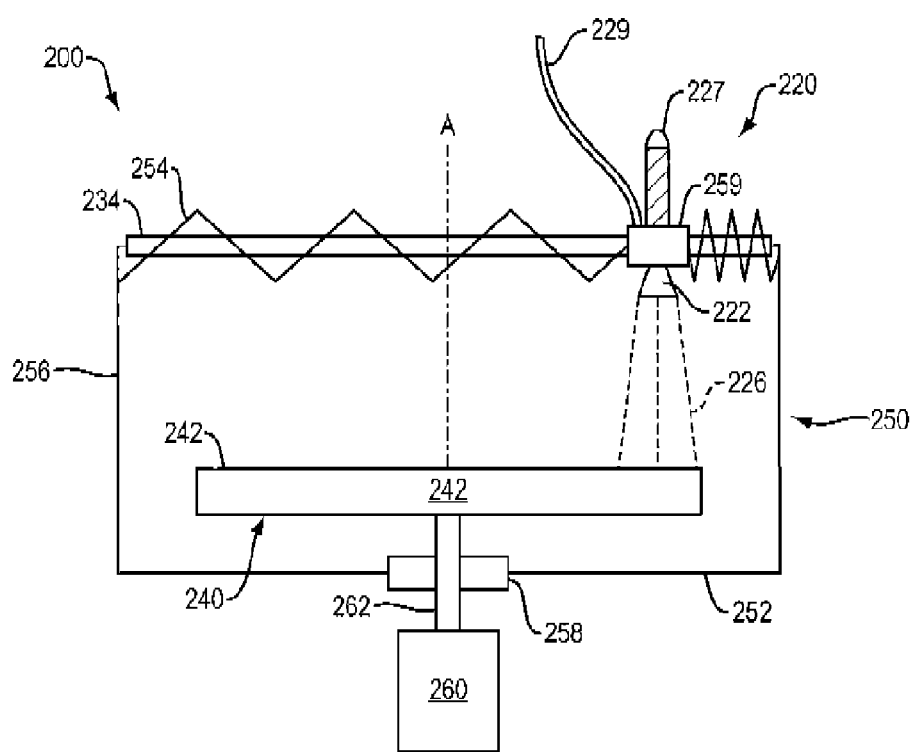
FIG. 2A is a schematic representation of an apparatus for dispensing particles contained in a liquid onto a rotating substrate, surrounded by an enclosure, according to this invention.
Figure 2B:
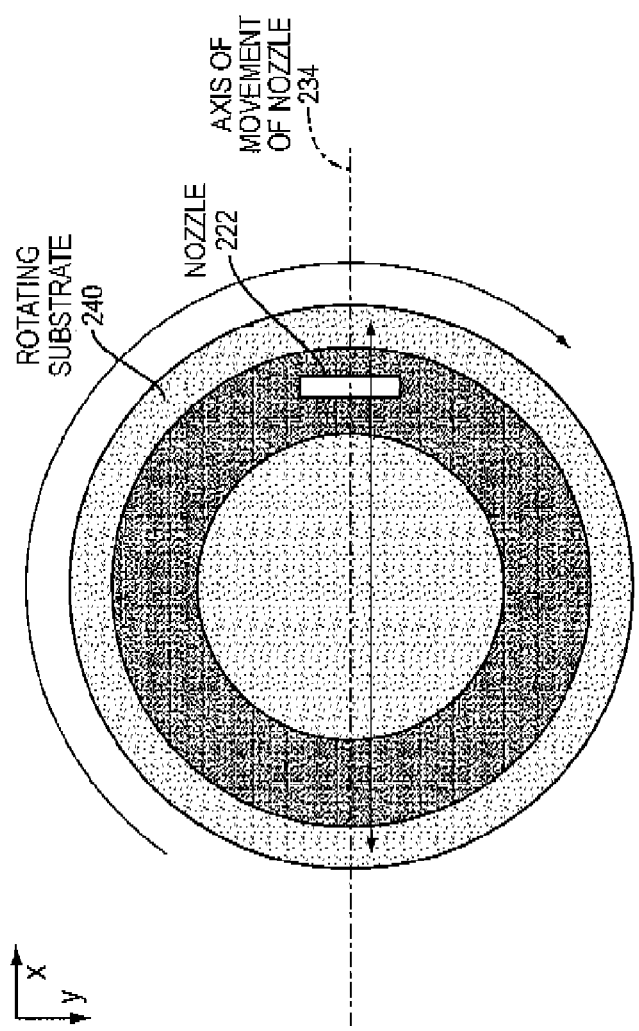
FIG. 2B is a schematic representation of an apparatus for dispensing particles contained in a liquid onto a rotating substrate, depicting lateral motion of the dispenser nozzle and rotary motion of the substrate, according to this invention.

It will be appreciated that various controlled movements of the particle dispenser and substrate can be used to achieve the desired uniform distribution on the substrate. With reference now to FIGS. 2A and 2B, another exemplary embodiment of apparatus 200 in accordance with the present teachings is depicted. The apparatus 200 of FIGS. 2A and 2B is substantially similar to that of FIG. 1 but differs in that the substrate 240 is configured to rotate about a central axis (A) substantially perpendicular to the surface 242 of the substrate 240, while the nozzle 222 of the sample dispenser 220 is configured to translate along a single axis (e.g., the x-axis). As shown in FIG. 2A, for example, the substrate 240 can be coupled to a motor 260 such that the substrate 240 can rotate as the nozzle 222 directs the spray 226 to the surface 242. Though the substrate 240 depicted in FIG. 2A is coupled to a shaft 262 of the motor 260, it will be appreciated that the substrate 240 can be releasably coupled to a motor 260 using a variety of configurations including any of mechanical, magnetic, or vacuum coupling, for example. By way of example, a vacuum can be applied through the shaft 262 to the bottom surface of the substrate 240. Alternatively, the substrate 240 can be disposed on a rotating platform, for example.

The exemplary particle deposition apparatus of FIGS. 2A and 2B can also provide movement of the nozzle 222 relative to the substrate 240. By way of example, in addition to the relative motion resulting from rotation of the substrate 240, the cell processing system can additionally include a scanner that is configured to translate the nozzle 222 along a guide member 234, for example. As shown in FIGS. 2A and 2B, for example, a controller (not shown) can be configured to control the scanner to slide and/or otherwise move the nozzle 222 along the guide member 234 over the surface 242 of the substrate 240.

With reference again to the exemplary particle deposition apparatus depicted in FIGS. 2A and 2B, exemplary relative motions of the nozzle 222 and substrate 240 will now be described in more detail. In one embodiment, the nozzle 222 can be moved radially (e.g., from the axis (A)) towards the periphery of the substrate as the substrate 240 rotates about the axis (A). In order to obtain a substantially uniform distribution as otherwise discussed herein, the dwell time for a nozzle 222 spraying a constant flow rate of the sample is proportional to the distance from the axis (A). That is, assuming a constant sample flow rate through the nozzle 222, the nozzle 222 will spend less time at the center of the substrate where there is less area to coat and more time at the periphery where there is more area to coat (larger circumference). Accordingly, as the nozzle moves outward as shown in FIG. 2B, its rate of lateral translation can be decreased. Alternatively, it will be appreciated that if the rate of lateral translation is held constant, the controller can increase the fluid flow of sample through the nozzle 222 with increasing distance from the axis (A). Alternatively the angular speed of the substrate can be decreased.

In some embodiments, the particle deposition apparatus 200 of FIGS. 2A and 2B can be used for dispensing one or more biological materials on multiple substrates or can be disposed of after a single use. For example, after delivering a biological material through the nozzle 222 to the substrate 240, the substrate 240 can be removed from the enclosure 250 for further post-deposition processing and the enclosure 250 and nozzle 222 (and any portion of the apparatus 200 that contacts the biological fluid) can be disposed of. Optionally, the substrate 240, enclosure 250, and nozzle 222 can be packaged (e.g., in paper, cardboard, plastic or a combination of these) and ready for sale to the end user such that the end user can simply couple the substrate 240 to the motor 260 and the nozzle 222 to an air supply 229 and a reservoir 227 containing the sample to be dispensed, for example. Additionally or alternatively, in some aspects, the apparatus 200 or portions thereof can be suitable for a limited number of uses and subsequent sterilizations, or can be a durable device suitable for many repeated uses and sterilizations. By way of example, all or a portion of the apparatus 200 can be sterilized by autoclaving, gamma irradiation, ethylene oxide sterilization, or sterilization by other gas or radiation means.

In various embodiments, the apparatus 200 can additionally include an enclosure 250 that substantially surrounds the substrate 240 and, if desired, the dispenser. The enclosure 250 can have a variety of configurations, but is generally configured to prevent the dispersal of an aerosolized fluid containing a biological material other than on the target substrate 240. As shown in FIG. 2A, for example, the enclosure 250 can define a chamber in which the substrate 240 is contained and into which the outlet of the nozzle 222 is directed.

The enclosure 250 can have a variety of configurations and can be composed of a variety of materials. By way of example, as shown in FIG. 2A, the enclosure can include a bottom endwall 252 disposed beneath the rotating substrate 240, a top endwall 254, and one or more sidewalls 256 extending therebetween. As shown in FIG. 2A, the bottom endwall 252 and sidewalls 256 can be substantially rigid, for example, while at least a portion of the top endwall 254 can be flexible (e.g., through material and/or structural properties) so as to accommodate motion of the nozzle 222, as otherwise discussed herein. Optionally included is a mechanism for exhausting, purging, or decontaminating the gaseous or aerosolized contents of the enclosure prior to opening the enclosure. Additionally, the bottom endwall 252 can define a collar 258 through which the shaft 262 is to be disposed for coupling to the substrate 240. The top endwall 254 has an accordion-like configuration and defines a port 259 that can be configured to couple to the nozzle 222. Accordingly, the flexible top endwall 254 can move (e.g., as bellows) as the nozzle 222 moves along the guide member 234. The enclosure can have a variety of configurations. In one aspect, the enclosure and substrate can be configured to be disposed of after a single use. In some embodiments, the enclosure can comprise a flexible material. In various aspects, a second port can be disposed in the enclosure. By way of example, an air supply conduit can extend through the second port, the air supply conduit being coupled to a dispenser disposed within the enclosure for dispensing the biological sample. In accordance with the teachings herein, the dispenser can dispense, for example, a biological sample comprising cells on the substrate so as to form a cellular monolayer on the surface.

Figure 2C:
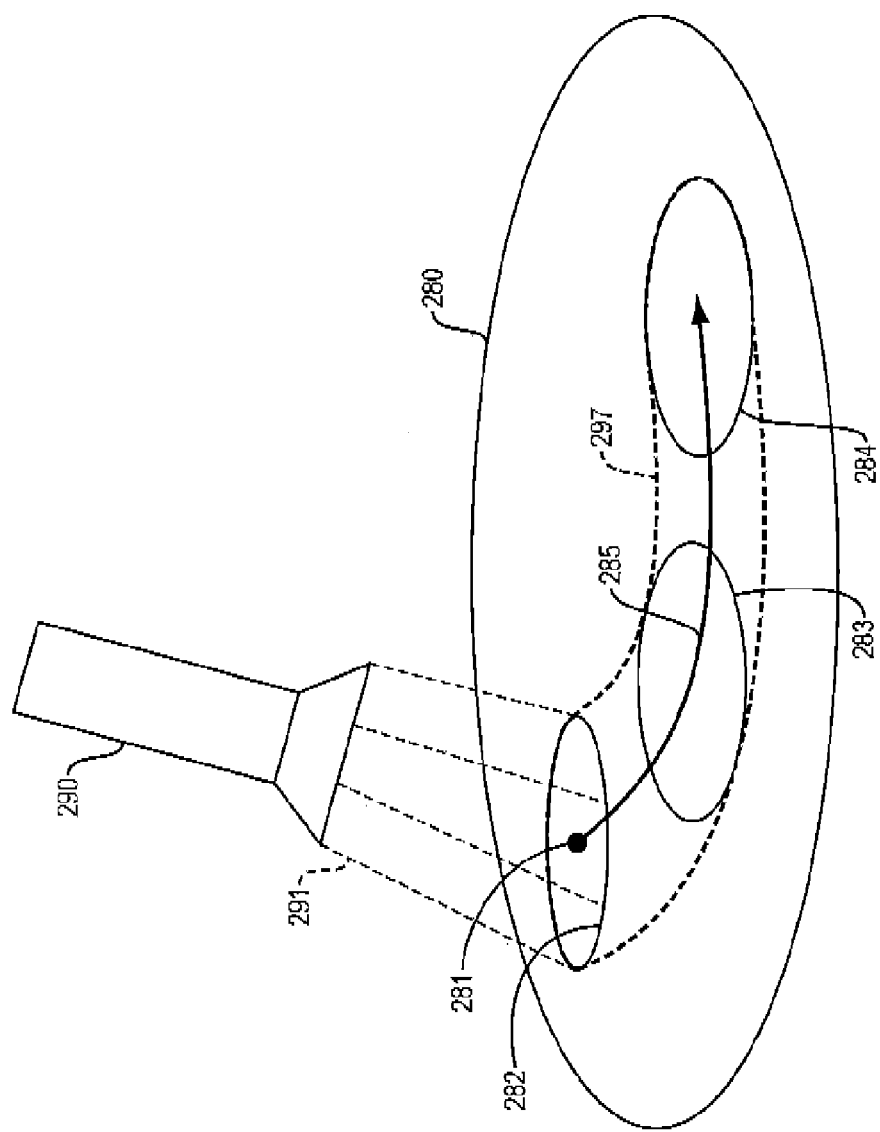
FIG. 2C is a schematic representation of an apparatus for dispensing particles contained in a liquid onto a substrate, depicting the trajectory of a movable target zone on the substrate, according to this invention.

FIG. 2C depicts dispenser 290 of particle dispensing apparatus 200 directing a spray 291 onto substrate 280. At an initial time $t_0$, the spray is directed to movable target zone 282, having a center 281. Relative motions of the dispenser and/or substrate direct the movable target zone along trajectory 285, such that at time $t_1$, the movable target zone is in position 283, and at time $t_2$, the movable target zone is in position 284. The trajectory is optionally controlled by a controller, not shown. The result of the passage of the movable target zone along the trajectory shown is deposition of spray droplets in deposition zone 297. The trajectory is preferably configured so as to extend the deposition zone to a substantial portion of the surface of the substrate. In some embodiments, trajectory 285 can be such that the movable target zone (or a portion thereof) passes over the same portion of the substrate more than once. In some embodiments, the movable target zone moves relative to the substrate because the substrate moves while the dispenser is fixed in position and orientation. For example, a rotating substrate and a fixed dispenser position will result in a circular trajectory of the movable target zone. A rotating substrate combined with a translating motion of the dispenser can result in a spiral trajectory. A wide variety of trajectories is possible.

In other embodiments, the trajectory of the movable target zone on the surface of the substrate results from the motion of the dispenser while the substrate is fixed. For example, a spiral trajectory of the movable target zone can result from the motion of the dispenser aperture in a spiral pattern in the x-y plane. Alternatively, a spiral pattern could result from the dispenser aperture rotating so as to direct spray at different angles toward the surface at a fixed location in the x-y plane.

Figure 3:
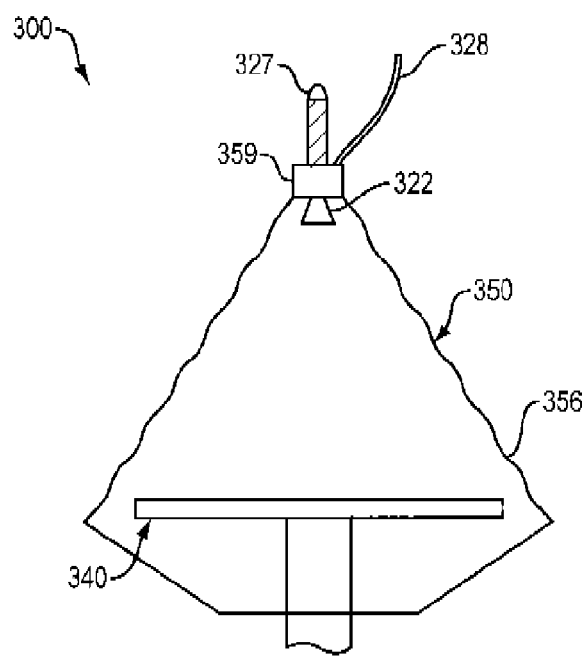
FIG. 3 is a schematic representation of another apparatus for dispensing particles contained in a liquid onto a rotating substrate having an enclosure, according to this invention.

With reference now to FIG. 3, another exemplary particle dispenser 300 in accordance with the present teachings is depicted. The apparatus 300 of FIG. 3 has sidewalls 356 substantially flexible to accommodate motion of the nozzle 322, which can be coupled to or extend through a port 359 formed in the top of the enclosure 350, and can be connected to an air supply 328. The nozzle 322 is configured to pivot to direct spray toward different regions of the substrate.

Figure 4:
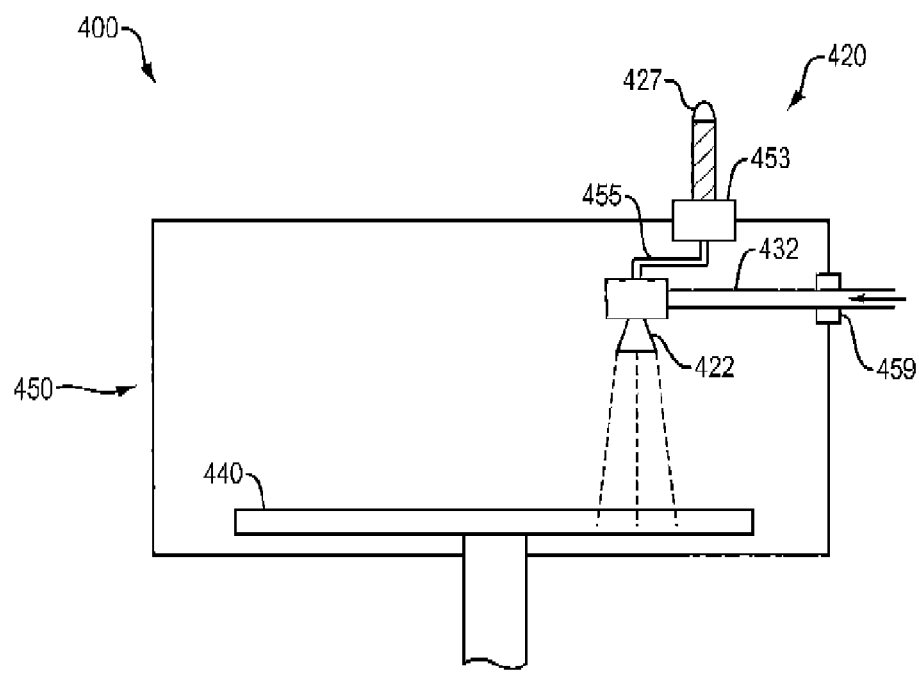
FIG. 4 is a schematic representation of another apparatus for dispensing particles contained in a liquid onto a rotating substrate having an enclosure, according to this invention.

With reference now to FIG. 4, another exemplary embodiment of a particle deposition apparatus 400 in accordance with the present teachings is depicted. The apparatus 400 has a top endwall containing a port 453 to which a reservoir 427 (e.g., specimen collection tube) containing a sample can be coupled, while the sidewall 450 contains a port 459 through which an extendable arm 432 of the sample dispenser system 420 can be disposed. As shown in FIG. 4, the extendable arm 432 can additionally include a lumen through which compressed air can be delivered to the nozzle 422 for aerosolizing the sample. As such, a sample contained within the reservoir 427 can be delivered to the nozzle 422 disposed within the enclosure 450 via a flexible tube 455, while the arm 432 can be extended so as to move the nozzle 422 (e.g., radially) over a rotating substrate 440.

It should also be appreciated that at least a portion of the apparatus 400 can be disposed of after a single use. By way of example, the substrate 440, sample reservoir 427, flexible tube 455, nozzle 422, and/or enclosure 450 can be disposed of after dispensing a biological material.

Sample reservoir 427 can optionally be a chamber in which a chemical reaction can be performed. For example, chemical or biochemical reagents can be added to the particle-containing liquid, so as to produce a reaction with those particles, prior to the particles passing to the dispenser for dispensing through the aperture onto the surface of the substrate. Optionally, a second chamber is provided for holding the chemical or biochemical reagent prior to addition to the reservoir. A valve or other structure can also be provided to gate the second chamber from the reservoir, or to gate the reservoir from a downstream portion of the dispenser.

As discussed above, systems in accordance with the present teachings can enable high-density, substantially uniform distribution of components of particles and materials on the surface of the substrate, such as for example, cells or beads. Moreover, by creating such a uniform distribution, various post-deposition processes can be utilized to analyze the cells or sub-cellular components disposed on the substrate.

Figure 5A:
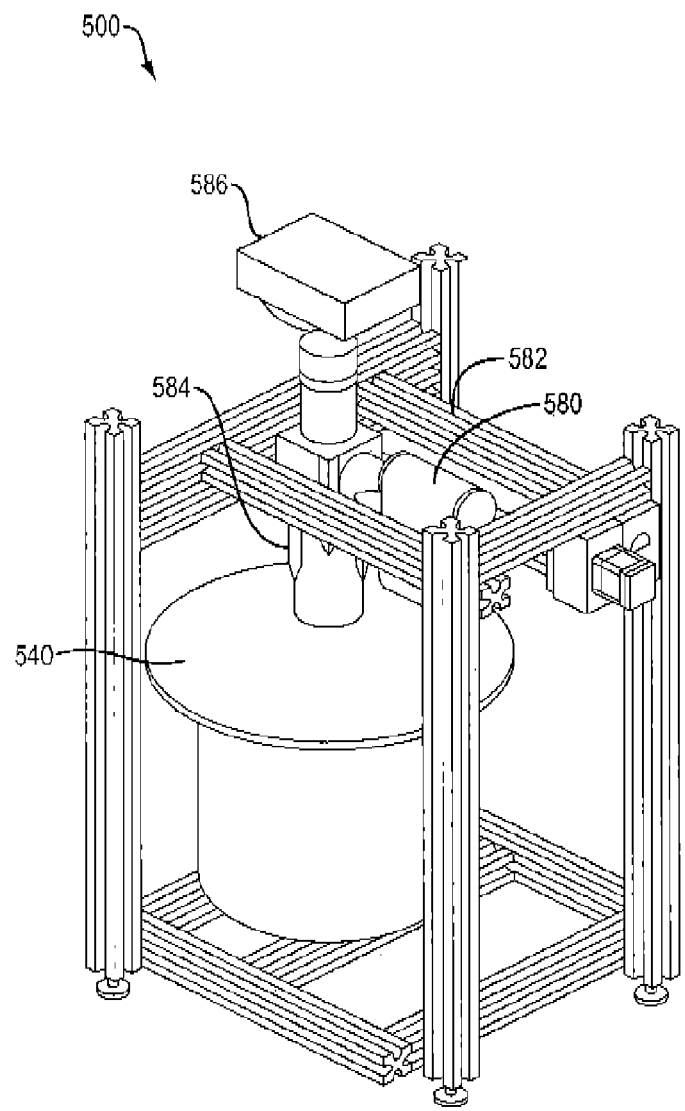
FIG. 5A is an illustration of an imaging apparatus in accordance with aspects of the present invention.

With reference now to FIG. 5A, for example, an exemplary apparatus, imaging device 500, enables the high throughput parallel analysis of particles (e.g., cellular and/or sub-cellular components) disposed on the surface of a substrate 540, as otherwise discussed herein. Though the apparatus 500 enables various post-deposition analyses on a substrate upon which the components of a biological sample are substantially uniformly distributed using exemplary deposition systems discussed above with reference to FIGS. 1-4, it will be appreciated that the particle, e.g., cell, processing systems can be integrated into a single system that enables both the deposition and post-deposition imaging and analysis.

As shown in FIG. 5A, the exemplary imaging device component 500 of the present invention can detect and/or image at least a portion of the substrate 540 having particles, e.g., biological particles such as cells, distributed thereon. Whereas existing technologies such as flow cytometry generally serially detect labeled cells of an enriched sample as the cells pass through a detector's field-of-view (FOV), imaging device 500 in accordance with the present teachings can be configured to parallel image the entire surface (or a portion thereof) of a substrate such that many components of a biological sample disposed on the surface as otherwise discussed herein are imaged simultaneously.

Figure 5B:
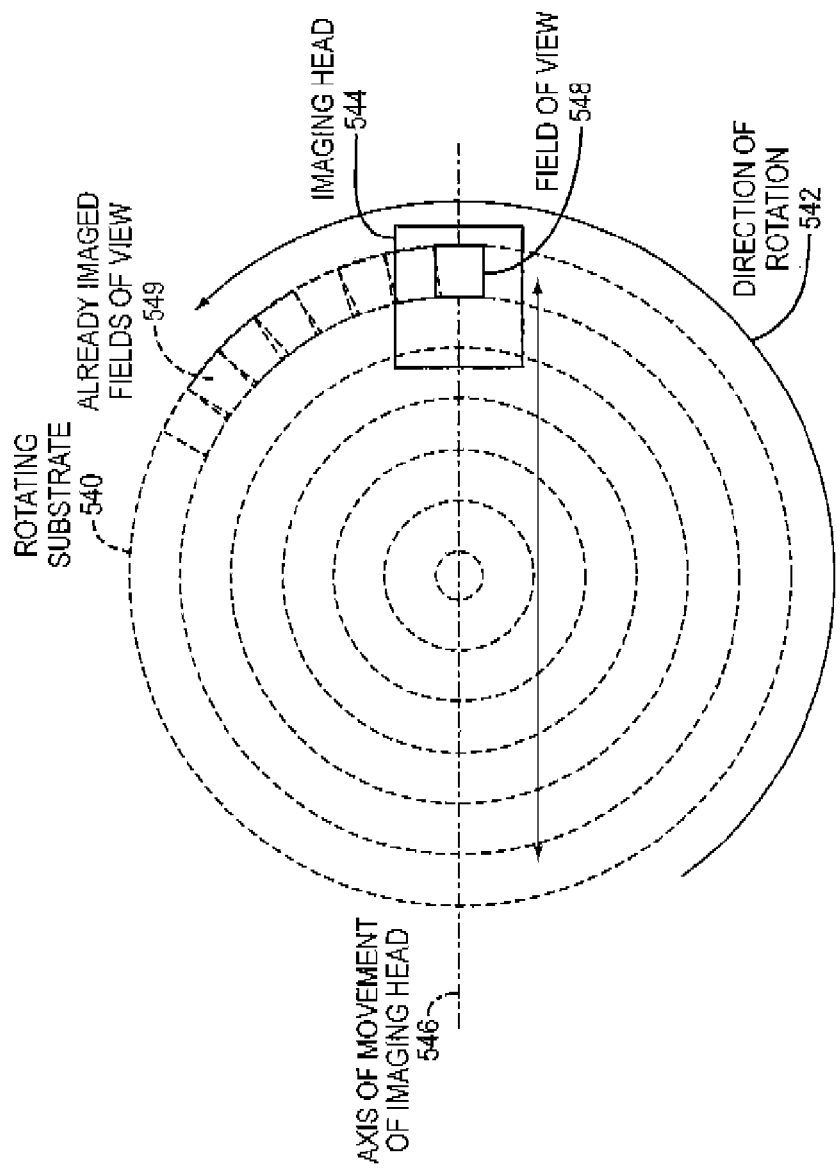
FIG. 5B is a schematic representation of a substrate, depicting the imaging of successive areas thereon in accordance with aspects of the present invention.

In a preferred embodiment, the principles and methods of cellular astronomy are used in the imaging process. As shown in FIG. 5B, substrate 540 can be rotated under imaging head 544 to image an active field of view 548. Owing to substrate rotation, successive fields of view can be imaged. Also shown is an already imaged field of view, numbered 549. Head 544 systematically examines the entire substrate, moving along path 546 as required. The motion of the imaging head can be controlled by a controller, which can optionally record the location of notable imaging events and save them to allow for subsequently returning to that field of view. In addition, the imager can permit zooming in, within a particular field of view, and can optionally allow for the recording of coordinates of regions of particles of interest, as well as recording magnification settings.

A variety of interrogation and detection techniques can be used in accordance with aspects of the present invention. These techniques include non-optical techniques, including for example, a parallel array of electronic or magnetic sensors properly positioned to capture and detect a signal from the sample.

The ability of the present methods and systems to facilitate the simultaneous processing of a large number of particles, such as cells, is significant. Parallel imaging methods such as cellular astronomy have significant advantages over sequential imaging techniques such as flow cytometry, as in the latter, there is a significant dead-time between receiving the signal of a cell and the signal of the subsequent cell due to their spacing. A goal of parallel processing methods such as cellular astronomy is increased speed of analysis. This goal of increased speed is facilitated by aspects of the present invention, including, for example, the ability to form monolayers with a high packing density, such arrangements of particles increasing the speed of analysis by decreasing the number of times it is required to shift field of view in order to scan the entirety of a given number of cells, beads, or other particles.

It will be appreciated that a wide variety of detection techniques known in the art and modified in accordance with the present teachings can be used to detect and/or image materials disposed on the substrate 540. By way of non-limiting example, optical, magnetic, electron, and scanning probe microscopy can be used to analyze a biological component disposed on the substrate. A wide variety of microscopes and microscopy techniques can be used, which can involve, for example, a wide range of magnifications; in embodiments, this can involve high magnification, low magnification, no magnification, or even the opposite of magnification (negative magnification). As will be appreciated by a person skilled in the art in accordance with the teachings herein, disposed materials such as biological particles can additionally be stained and/or labeled by associating the sample with a probe (e.g., fluorescent microbeads) before and/or after depositing the biological sample on the substrate 540. In various aspects, excess probe molecules need not be washed away prior to imaging the substrate 540.

In this and in other embodiments of the invention, it is preferred, but not necessary, that the detection system both have the resolution and sensitivity to interrogate and to detect individual particles. Instead of interrogating individual particles, groups or regions of particles can be interrogated, analyzed, imaged, or detected, yielding, for example, information about average properties of the region, or whether or not a particular signal (e.g., nuclear emission) is emanating from the region, regardless of whether the system is capable of identifying the particle from which the signal emanates. In such a case, where a particular event is detected in a region, the particles from that region can optionally be subjected to further interrogation by methods having greater sensitivity, resolution, or both.

It should be further appreciated that biological particles and biological capture beads deposited on substrates according to aspects of the invention can be manipulated following deposition on the substrate surface. The manipulation can take a variety of forms, including extraction of a subcellular component, such as a cell nucleus, or contacting one or more biological particles with reacting molecules, such as protein molecules, polysaccharides, lipids, and nucleic acid molecules. Biological particles and biological capture beads can also be extracted from the surface and optionally examined in further studies.

As another example, cells in spin-brushed monolayers can be further interrogated after cellular astronomy analysis. After deposition onto a substrate, cells or other particles (e.g., biological particles) can be re-interrogated with high-resolution microscopy and can be physically isolated for down-stream analysis. Physical isolation can be performed with a micro-manipulator and other approaches including laser-capture microdissection.

The exemplary system 500 of FIG. 5A, for example, can be configured to detect the light transmitted through the sample disposed on the substrate 540. The system includes a light source 580, optics 584 (e.g., one or more filters and/or lenses), and a detector 586 (e.g., CCD detector).

In such an exemplary embodiment, light generated by the light source 580 can be collimated to illuminate all or a portion of the substrate 540 such that emitted light passes through the objective 584 (optionally, with zoom) and is imaged by the detector 586. The optical system is mounted on a linear slider. Because of the substantially uniform, high density of the deposited particle, e.g., cells, the detector 586 can interrogate a large number of particles simultaneously. One type of imaging that can be used with the present invention is epi-fluorescence optical microscopy. Different illumination schemes are within the scope of the invention, including trans-illumination, oblique illumination, and epi-illumination.

By way of example, more than $10^6$ cells, and in some aspects more than $10^7$ cells, deposited on the substrate in a cellular monolayer can be imaged simultaneously and analyzed using image analysis techniques known in the art and modified in accordance with the teachings herein. A preferred sequence of image analysis techniques consists of the following steps: image background estimation (low image frequencies); background subtraction; image filtering to enhance events; image thresholding; connected component analysis; component disambiguation, e.g., splitting several events that form the same component; and individual event analysis to test for the presence or absence of a given biomarker.

Moreover, the system 500 can include a controller (not shown) that can be configured, for example, to control the system 500 to further inquire about an area of interest. By way of example, should an area of the substrate 540 indicate the presence of a target cell or cellular component, the controller can automatically control a scanner (not shown) and/or optics 584 to zoom in on that particular portion of the substrate 540 for further imaging. The optical system can also be configured to scan several fields of view of the substrate. Such scanning can be achieved by rotating the substrate and moving the optical system linearly, similarly to the movement of the dispenser In one embodiment, the optical system will image at least one field of view to test for the presence or absence of at least one biomarker. If several fields of view are taken, the fields of view can be registered to form a larger image of the scanned sample. Such registration can be done by stitching the images of different fields of view using the information of the borders or by using fiduciary biomarkers installed into the spread biological sample, or placed beforehand on the substrate. The optical system can subsequently switch at least one filter and optionally the illumination source to test for the presence of a second biomarker in at least one field of view previously sampled. The images obtained for several biomarkers are then registered (i.e. aligned) so that the presence or absence of biomarker expression in a given pixel coordinate of the images correspond to the same underlying physical event. The registration can be done using the statistics of the sample (how many events will show biomarker expression in different channels) or the installed fiduciary points. In other embodiments, the optical system will test the presence of at least one biomarker in the field of view. If present, the system will change the filters to test for the presence of a second biomarker. Then the system will change the field of view.

Figure 5C:
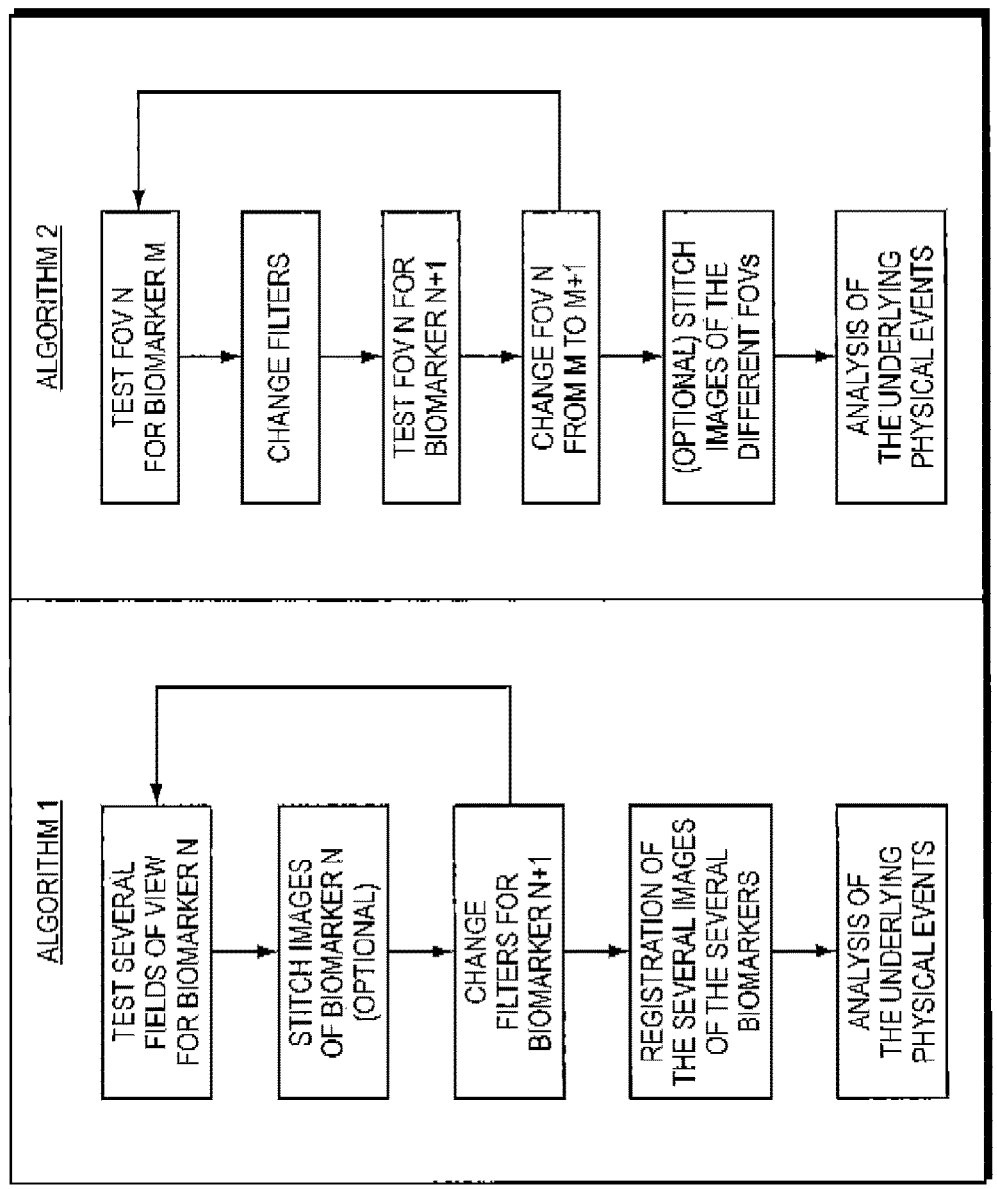
FIG. 5C is a pair of algorithms for image processing in accordance with aspects of the present invention.

Additional information regarding an algorithm that is useful in connection with aspects of the claimed invention is shown in FIG. 5C.

In combination some methods and systems in accordance with the present teachings can enable the deposition of particles, such as biological particles without particle selection (and thus, minimal cell loss) and rapid, sensitive parallel imaging. Accordingly, the exemplary methods and systems in the present teachings can enable detection of rare cells and the unbiased analysis of cell demographics within a large cell population. By way of example, although circulating tumor cells (CTCs) can be extremely rare (e.g., less than 1 CTC per $10^9$ blood cells), methods and systems in accordance with the present teachings can rapidly determine the presence of a single rare event by acquiring a whole blood sample, depositing the sample on a substrate in a dense, uniform monolayer without attempting to selectively enrich the sample, and examining the monolayer via optical techniques in accordance with the teachings herein. For example, an aspect of one such technique would be scanning several fields of view ("FOV") of the sample with the optical system, e.g., with approximately 500 FOV to test 1 billion cells with a 4 megapixel camera.

The present teachings can additionally enable the detection of such rare events such as cancer stem cells, bacteria, viruses, circulating epithelial cells, mesenchymal stem cells, and fetal red blood cells, all by way of non-limiting example. It will also be appreciated that by generating one or more substantially uniform layers of a biological component (e.g., which can be associated with a fluorescent probe molecule), the presence and/or quantity of the biological component can be determined using image analysis techniques. Additional exemplary quantitative techniques include quantitation of HIV CD4+, leukemia phenotyping, and diagnosis of cancer, including peritoneal cancer. Moreover, the above-described systems and methods can be useful in drug development, monitoring treatment efficacy, dynamic rare cell studies, and/or rare cell isolation and culture.

The combination of spin-brushing and cellular astronomy allows cells and molecules to be interrogated, detected, quantified, and/or analyzed. In a cellular array embodiment, the molecular expression (e.g., antigen expression) of cells can be visualized and correspondingly quantified/digitized. As every cell will correspond to a particular location on the substrate, further isolation and analysis can be carried out on desired cells in the array.

Likewise, the combination of spin-brushing and cellular astronomy can be used in addition to molecular recognition (micro)beads with a molecular diagnostics array. For instance, a fluid containing an analyte/biomolecule can be mixed with molecular recognition beads that have bound reporter beads, and this mixture can be spin-brushed onto a surface. Cellular astronomy can then be used to analyze the beads for molecular recognition and reporting events, thus constituting a (bio)molecular array.

Other examples can be the use of the system as a planar flow cytometer to study relative populations of cells. Various methods and systems in accord with the invention can dispense a biological sample on the surface of the substrate so as to form a substantially uniform layer on the substrate so as to enable rapid, simple, and sensitive detection of cells and/or sub-cellular components (e.g., proteins, biomarkers), with limited or no selective cell loss or sample enrichment prior to deposition.

EXAMPLES

Figure 5D:
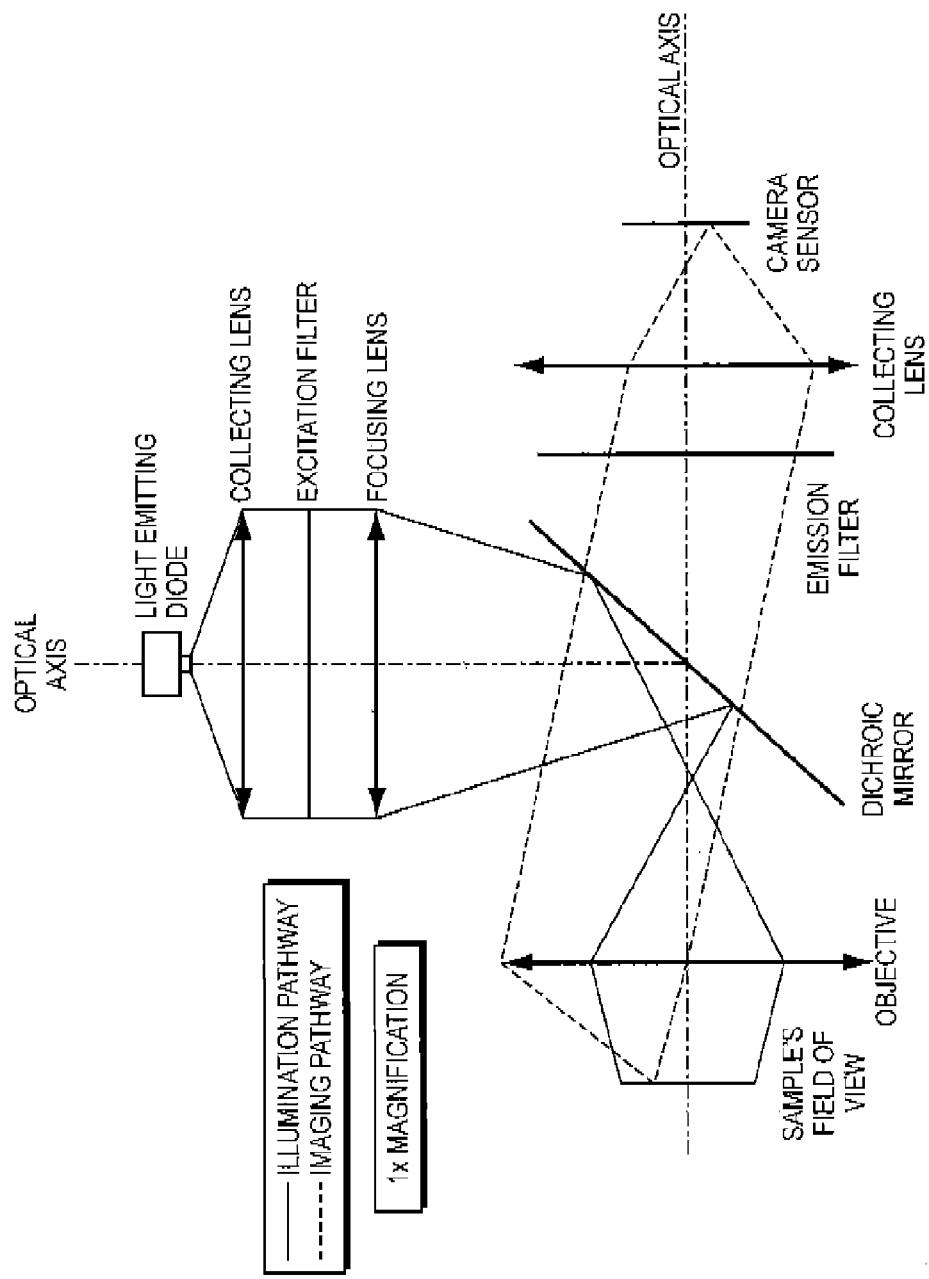
FIG. 5D is a schematic representation of an imaging system in accordance with aspects of the present invention.

The schematic design of the epi-fluorescence microscope used in connection with embodiments of the present invention is shown in FIG. 5D.

In one experiment in accordance with aspects of the present invention, a hydrophilic Petri dish was rotated while having a whole blood sample aerosol sprayed thereon (spin-brushing). Various portions of the resulting dish surface are shown in FIG. 6. A person skilled in the art will appreciate that each of the edges, center, and portions of the Petri dish therebetween exhibit a substantially uniform cell-packing density and distribution. The cell-packing density could have been modulated, as desired, by adjusting the spray time, the rotation speed and/or the speed of the relative movement of the nozzle and the substrate, and/or the dilution of the sample.

In a second experiment in accordance with aspects of the present invention, a cellular monolayer was prepared by spin-brushing. Using a commercial airbrush, 20-1000 uL of whole or diluted blood was dispersed in an aerosolized form over a spinning substrate (~50-500 rpm) or a stationary substrate. The motion of the airbrush was either translational in one direction or was back-and-forth to recoat the same area. The areas coated ranged from a glass microscopy slide to an overhead transparency. The total spray time and volume deposited were proportional to the area.

Figure 7:
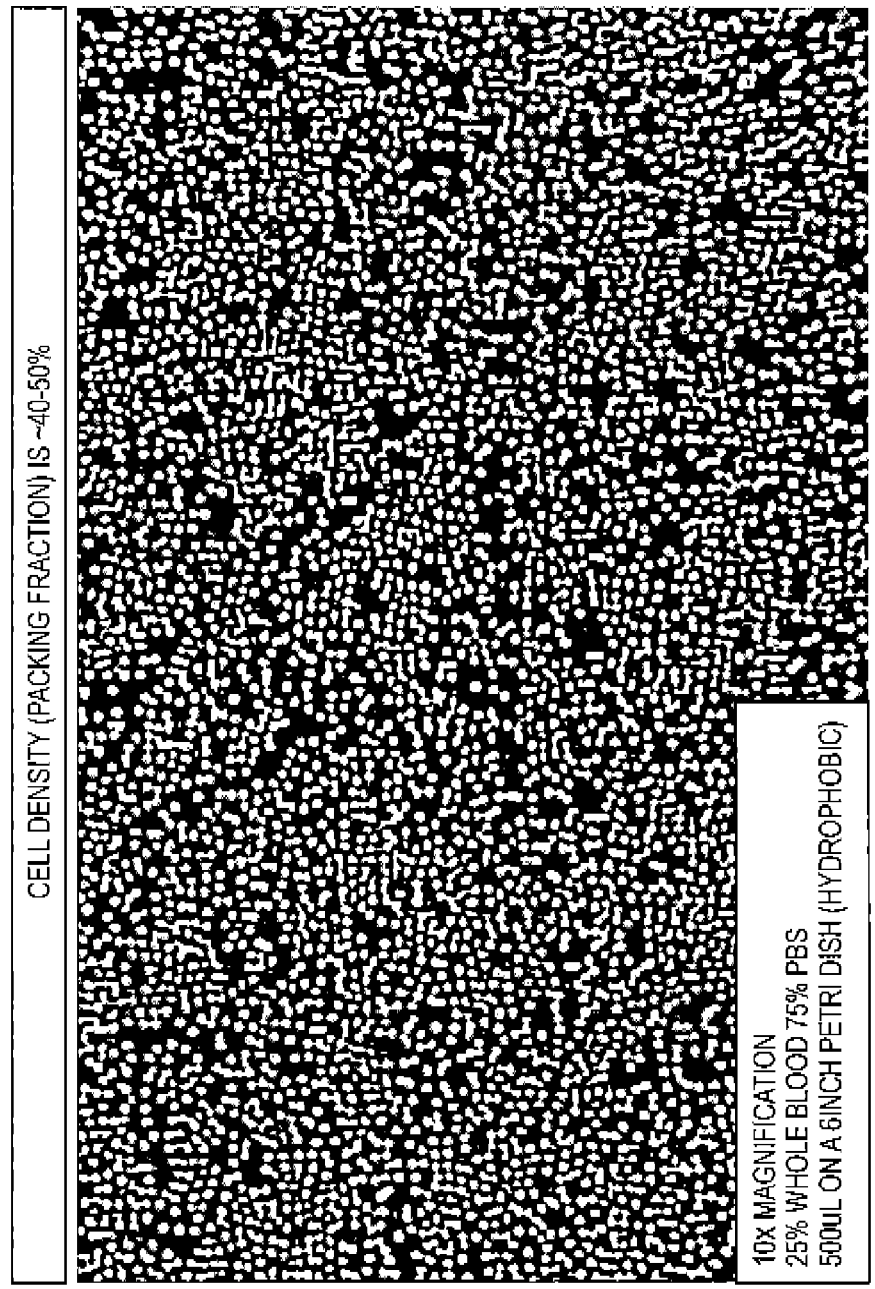
FIG. 7 depicts another exemplary distribution of cells dispensed onto a substrate in accordance with aspects of the present invention.

In a third experiment in accordance with aspects of the present invention, a 6-inch Petri dish having a relatively hydrophobic surface was rotated at a speed between 100-300 rpm, while an aerosol dispenser sprayed 500 uL of a biological sample containing 25% whole blood and 75% PBS at various radial positions. FIG. 7 depicts the results of the experiment at 10× magnification, showing a cell-density of about 40-50%, and having a substantially uniform distribution.

In a fourth experiment, cell monolayer uniformity and density were quantified. Materials for the experiment included swine blood (1 month old, obtained from Lampire) and 3-inch Petri hydrophobic dishes (plasma treated, obtained from BD Falcon).

The 3-inch Petri hydrophobic dishes were pre-treated with 200 uL of 1% glycerol in DI-water for a few minutes, and then shaken dry, to render the surface hydrophilic. Diluted blood solution was prepared with 2 mL of swine blood, 3.4 mL PBS, 700 uL glycerol, and 1 mL blue dye (500 mg/2 mL). The glycerol (10% overall) was used to increase the viscosity of the solution and to decrease the rate of drying after deposition. The dye was used to darken the background and highlight the cells for automated segmentation.

Figure 8:
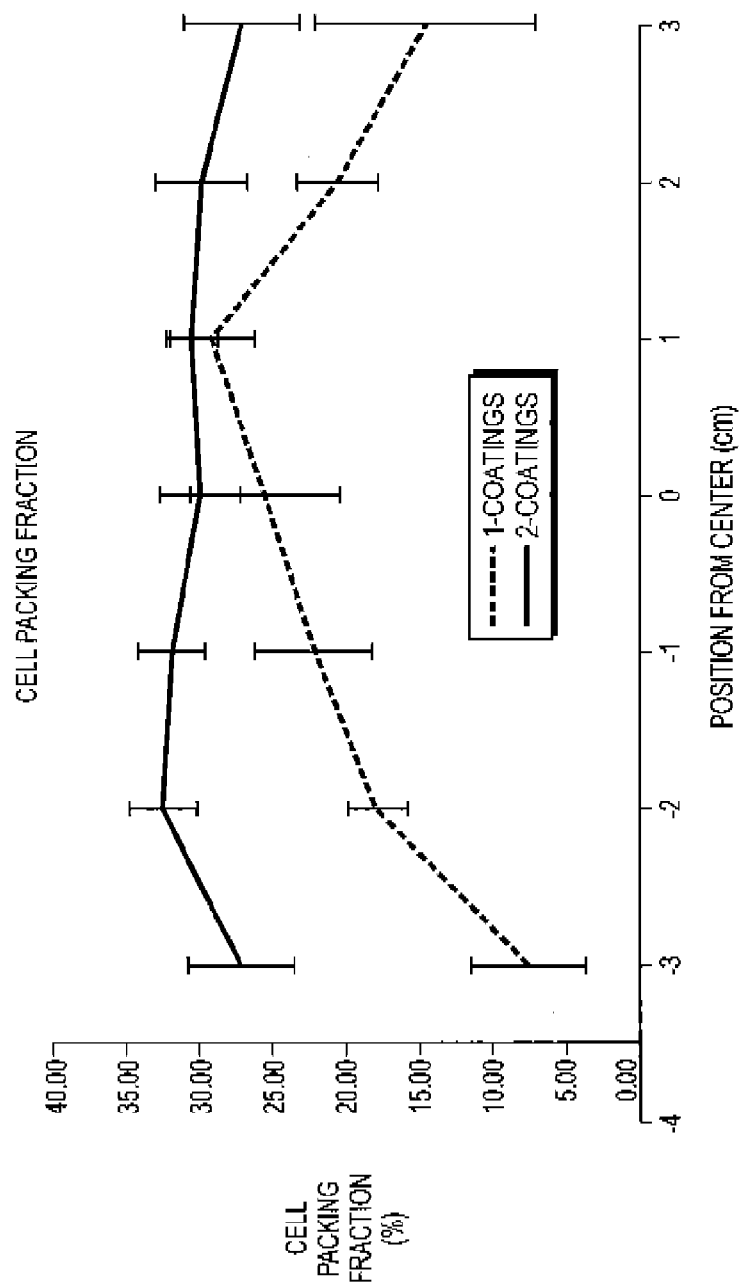
FIG. 8 is a graph showing packing density of cells dispensed onto a substrate in accordance with aspects of the present invention.

Diluted blood solution was deposited onto the Petri dish substrates through the aerosolizer nozzle (1 full rotation open) either with one or two complete lateral passes over the rotating dishes. After deposition, cells were allowed to settle for 10 minutes and then imaged at 10-20× magnification; imaging was performed at different points along the Petri dish. Afterwards, cells were algorithmically segmented and extracted from the background to yield the cell packing fraction, which is plotted in FIG. 8 as a function of position, measured as centimeters from the center of the Petri dish. Separate curves are given for one and two coatings applied.

Figure 9:
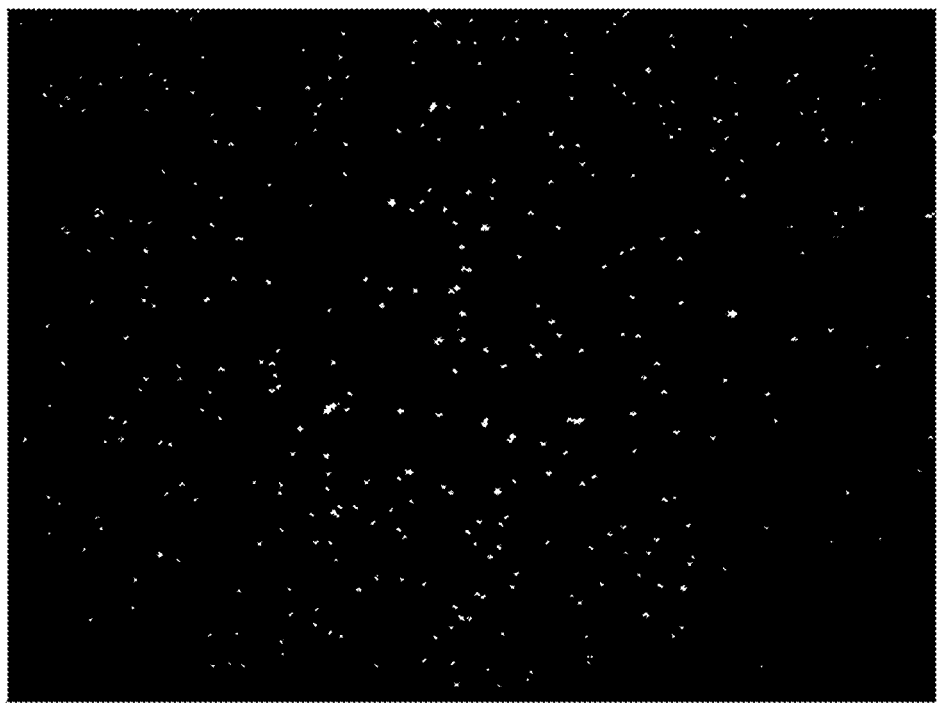
FIG. 9 depicts the fluorescence signal obtained from cells that were dispensed onto a substrate in accordance with aspects of the present invention and marked with a biomarker.

In a fifth experiment in accordance with aspects of the present invention, human blood was spin-brushed onto a hydrophilic Petri dish after having been stained with FACSCount (from BD BioSciences, Becton Dickinson) reagent for CD3/CD4, and imaged using the epi-fluorescent microscope of FIG. 5D. Similar experiments were performed with swine blood and Streck cells. FIG. 9 shows a representative image of a fluorescently labeled cell monolayer imaged at low-magnification.

In additional experiments in accordance with aspects of the present invention, porcine peripheral blood (Innovativeresearch, Novi, ML), was used either undiluted, or diluted with PBS to final concentrations ranging down to 10% of the original blood concentration. An aliquot of 100 uL-1 mL of this mixture was loaded into an apparatus for deposition, using a commercial airbrush. In subsequent experiments, flow cytometry calibration microbeads with fluorescent intensity equivalent to immunofluorescently-labeled cells (~7 um, Bangs Laboratories, Fishers, Ind.) were spiked into the blood mixture at various titrations. Typically, microbead final concentration was equivalent to the white blood cell concentration ($10^6$ events per 1 mL).

In a biosafety hood at room temperature, the fluid was dispersed in an aerosolized form over a stationary or spinning substrate (~50-500 rpm). The flow rate of the apparatus was held constant by the nozzle opening and air pressure. During this time, the nozzle was moved continuously in relation to the substrate in a back-and-forth or raster motion over the span of 5-60 s. The total spray time and volume deposited were proportional to the area.

Monolayer samples from aerosolized deposition or blood smears drawn by standard techniques were subsequently imaged at ~1× (test case) and 20× (reference standard) magnification using a commercial fluorescent microscope or at ~1× using a self-built cellular astronomy microscope. After algorithmic extraction from the background, the detected events (e.g. beads, OVCAR5 cells (ovarian cancer cells, NIH, National Institutes of Health), dye-labeled cells, or immunofluorescently-stained mouse cells) were compared to the reference standard.

In an additional round of experiments, 200,000 OVCARS cells were incubated with CalceinAM at 1 uM, 0.1 uM, 0.01 uM, 0.001 uM, and 0 uM at 37 C for 30 minutes to perform cell-labeling. After washing and redispersion into PBS, the cells were deposited onto Petri dishes and allowed to settle prior to imaging.

Yet in another round of experiments, anti-Ly-6G (FITC)/anti-CD45 (pycoerthrin) labeled mouse tumor cells, human blood surrogate CD-Chex cells (Streck, Omaha Nebr.) labeled with anti-CD45-Cy5/anti-CD4-FITC following standard staining protocols (5 uL antibody per $10^6$ white blood cells), or 50 uL of anti-coagulated (EDTA, 10 min.) human blood labeled with ~375 uL of BD FACScount reagent after one hour of vortexing were imaged. After cell staining, the mixture was spin-brushed or smeared onto glass slides or Petri dishes. Samples were imaged immediately (wet or dry) or after allowing the cells to settle (wet or dry).

In these and various experiments, the materials used for substrates were Petri dishes, including 1, 3, and 6 inch hydrophobic and tissue-treated hydrophilic dishes, 8, 10, and 14-inch acrylic disks cut out of acrylic sheets, and glass slides and transparencies, cleaned with DI-water and ethanol prior to use.

The cell dispenser included a substrate movement device and an aerosolizer. The substrate movement device was either a commercial spin-coater intended for use in integrated-circuit wafer processing or a specially built spin-coater, using a CPU-fan and circuit modified to act as a spinning substrate/substrate support, and the motorized spinner. The aerosolizer was an airbrush. Both standard single-control (siphon-feed, control fluid rate) and dual-control (gravity feed, control fluid and air rate) were used.

Blood was either anti-coagulated whole swine blood (K2 EDTA) or human blood. Typical dilutions ranged from 20% to 100% final concentration of whole blood. The buffer was phosphate buffered saline.

Particles used were cells and cell-surrogates. Cell-surrogates were fluorescent microbeads such as 7-micron FITC and Texas Red beads with fluorescent intensity mimicking immunofluorescently-stained cells. Cells included OVCAR5 ovarian cancer cells, used to establish that cells could be seen with our device. In addition, commercial preparations of fixed white bloods cells used as flow cytometry standards (Streck CD-Chex Plus) were used as a safe alternative to human blood.

Fluorescent-antibodies were Anti-CD45 and anti-CD4 antibodies used to specifically label cells. A CD4+/CD3+ staining kit (BD FACScount) kit was used to stain non-fixed human blood and stabilized human cells (Streck cells). CalceinAM dye was used to non-specifically label cells. Giemsa-Wright stain was used to stain white blood cells in swine whole blood.

Imaging was performed with a commercial fluorescent stereomicroscope: The microscope had standard filter sets and a wide-field low-magnification objective with 1.2× and 20× magnification and a mercury burner illumination source.

Imaging was also performed with home-built cellular astronomy microscopy equipment. A custom microscope was built to detect particles (beads and cells). The key parameters of the microscope design were: high numerical aperture (>=0.25) and large field of view (1.5×1.5 cm). The epifluorescence microscope was configured with an excitation filter, a dichroic mirror and an emission filter. All filters are in infinite spaces. The illumination source was a commercial high power LED with a broad spectral band.

Algorithms for image processing included the following steps for the automatic detection of events: (1) Acquisition of dark frames to estimate the dark current and read out noise of the camera, and estimation of the average of such dark frames ($\delta$); (2) Optional acquisition of a flat field to estimate the illumination power in each pixel ($\xi$); (3) acquisition of the image (I); (4) subtraction of the average dark frame to the image, resulting in the corrected image $I=I-\delta$; (5) optional division of the pixel values by the flat field image according to the formula $I=I/\xi$; (6) estimation of the low level frequencies of the image by blurring it with a Gaussian kernel of high variance according to $I_L=I*g_o$, where * denotes convolution and g, the Gaussian kernel; (7) subtraction of the low level frequencies from the image according to $I_H=I-I_L$; and (8) estimation of the regions of the images containing events by convolving the image with a blob-finding kernel with a size corresponding to the objects to be detected, where such kernel can be the Laplacian of Gaussian (log), and in the case of several size objects, a multi-scale image filtering approach was used: $I_f=I_H*h_o$; (9) applying a threshold to the image to obtain pixels that are likely to be events. $I_t=I_f/I_f>t$; (10) finding connected components in the thresholded image, namely $I_c$; (11) optionally examining the connected components by their size, and if they are higher than the expected object size, splitting them according to a maximum likelihood criteria or rejecting them; and (12) establishing the fluorescence of the objects based on the ADU of the connected component.

In additional experiments, cell astronomy was performed using cells deposited according to aspects of the present invention and the results were compared with results obtained using flow cytometry. The experimental details are as follows:

Fixed peripheral blood was purchased from Streck. The Streck sample contained standard cell populations and subpopulations found in peripheral blood such as CD3+, CD4+, and CD8+ cells. Immunofluorescent labeling of the CD3+/CD4+ and CD3+/CD8+ subpopulations was performed using separate Beckton Dickinson FACSCount staining kits. The pre-mixed staining kit contained fluorescently-labeled antibodies against CD3 and CD4, or CD3 and CD8, in addition to dual-labeled fluorescent beads used for fluorescent gating. The staining was followed in accordance to the FACSCount product instruction sheet.

In some cases the cells in the Streck sample (Streck cells) were concentrated prior to addition of the FACSCount staining kit. After the staining incubation period, 3 uM DAPI (4',6-Diamidino-2-Phenylindole, Dihydrochloride) diluted in PBS was added to the mixture to for nuclear staining. Additionally, 100% glycerol was added to the biological mixture (final concentration ~10%).

The biological mixture was then spin-brushed onto glass slides taped to the substrate or Petri dishes. After deposition, cells were allowed to settle for 15 minutes and then imaged at ~1× with the Cell Astronomy Microscope and later at 20× on a TissueFAXS microscope with PE and PE-Cy5 filter cubes.

The resulting images were processed to detect and classify cells according to their immunofluorescence to generate dot plots. The generated dot plots were compared to dot plots obtained from similarly prepared samples which were analyzed with a commercial flow cytometer.

Figure 10A:
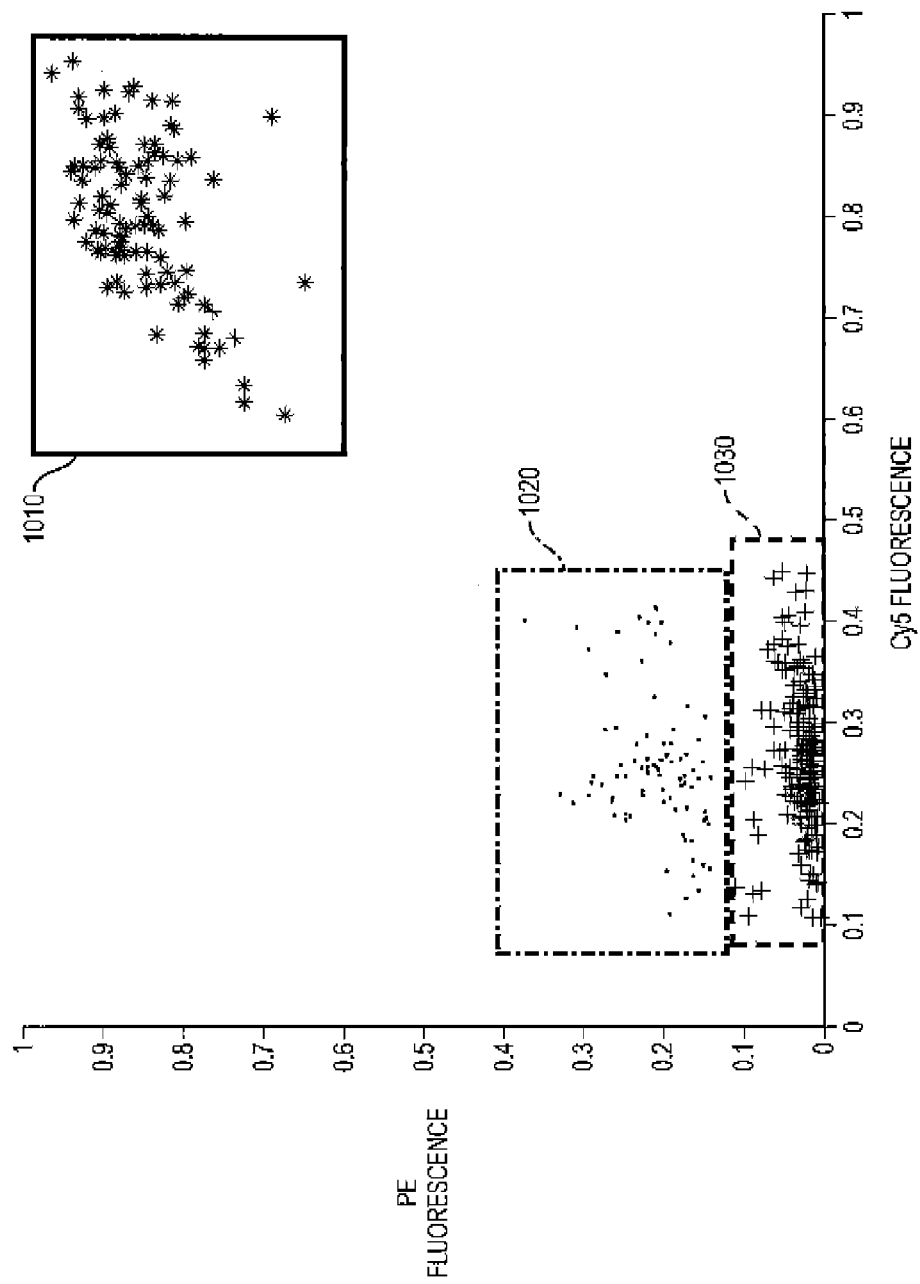
FIG. 10A is a dot plot of fluorescence-labeled cells and particles deposited onto a substrate.

The spin-brushing and cell astronomy approach was demonstrated to be qualitatively similar to the data from the flow cytometer. FIG. 10A depicts the dot plot of CD3 vs. CD8. (The characteristic dot plot for CD3+/CD4+ or CD3+/CD8+ cells would be expected to be similar). In FIG. 10A, fluorescence signal intensity from CD3 staining is shown on the x-axis, and from CD8 staining, on y-axis. FIG. 10A shows three clusters of fluorescent particles: cluster 1010, which corresponds to stained beads; cluster 1020, which corresponds to CD3+/CD8+ cells, and cluster 1030, which corresponds to CD3+/CD8− cells.

Quantitatively, the results of cellular astronomy on cells as prepared and deposited as described above, in accordance with aspects of the present invention, yielded a ratio of CD3+/CD8+ to CD3+/CD8− that was 94% of the ratio obtained by flow cytometry.

These data show that, in accordance with aspects of the present invention, cells can be deposited on a substrate, florescence information can be extracted from the deposited cells, and the extracted fluorescence information can be used to analyze, categorize, and classify cells, such as into the clusters 1020/1030 shown in FIG. 10A.

Figure 10B:
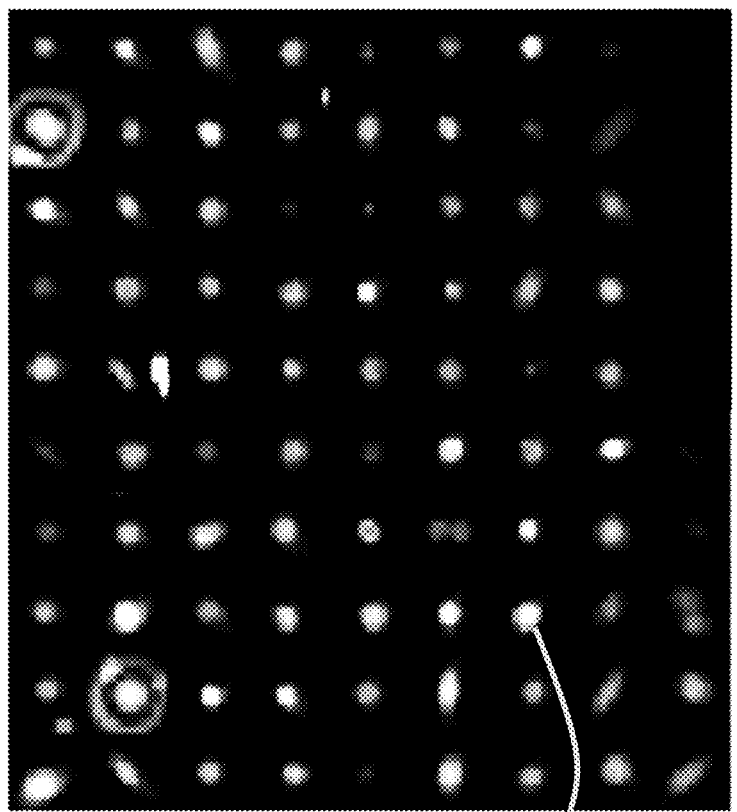
FIG. 10B depicts images of cells arranged in an array for inspection; these images correspond to cells in one cluster of the dot plot of FIG. 10A.

Further, as described below, cell information was associated with substrate coordinates in a manner that could permit further interrogation of cells of interest. FIG. 10B depicts image array 1070, which shows an array of images for the particles classified into cluster 1020 of the dot plot of FIG. 10A, namely CD3+/CD8+ cells. Image array 1070 includes, for example, cell image 1072. The displayed cells were linked to their recorded coordinates in a manner that could allow for further interrogation of selected cells (e.g., the cell corresponding to cell image 1072) in the imager with higher magnification.

The relevant teachings of all patents, published applications and references cited herein are incorporated by reference in their entirety.

While this invention has been particularly shown and described with references to example embodiments thereof, it will be understood by those skilled in the art that various changes in form and details can be made therein without departing from the scope of the invention encompassed by the appended claims.

What is claimed is:

1. A method for inspecting biological particles disposed within a liquid solution, comprising the steps of:
    introducing a liquid solution comprising the biological particles into a biological particle dispenser wherein the dispenser is an aerosolizer or nebulizer and is capable of translation along a dispenser travel path;
    dispensing the liquid solution, in an aerosolized state, toward a movable target zone on a planar surface of a substrate rotating around a rotational axis perpendicular to the planar surface, said movable target zone having a center;

guiding the center of the movable target zone along a radial path between the rotational axis and the periphery of the substrate on the planar surface while the dispenser is dispensing the biological particles and moving the dispenser along the dispenser travel path, the dispenser travel path being parallel to the radial path, so as to produce a two-dimensional pattern of the biological particles deposited on the planar surface of the substrate; and inspecting at least a portion of the biological particles deposited on the planar surface of the substrate.

2. The method of claim 1, wherein the aerosolizer is a spray brush.

3. The method of claim 1, wherein the radial path of the movable target zone defines a deposition area, and wherein the dispersion rate, dispersion location, dispersion pressure, and relative motion of the substrate and dispenser are controlled to achieve a packing density of the biological particles greater than 70% over the deposition area.

4. The method of claim 1, wherein the radial path of the movable target zone defines a deposition area, and the biological particles are deposited in a monolayer over the deposition area.

5. The method of claim 4, wherein the biological particles are cells.

6. The method of claim 5, wherein the inspecting comprises imaging the cells.

7. The method of claim 6, the inspecting further comprising using a CCD detector.

8. The method as claimed in claim 7, wherein the CCD detector uses a magnification of less than about 4 times.

9. The method of claim 1, wherein for each position of the dispenser along the dispenser travel path, the dispenser and the center of the movable target zone are radially displaced from the rotational axis by a same distance.

10. The method of claim 1, further comprising adjusting, dependent upon the position of the center of the moveable target zone along the radial path, at least one of a rate of dispensing of the liquid solution and a rate of translation along the radial path in order to maintain a uniform distribution of the biological particles deposited on the planar surface of the substrate as the distance from the center of the movable target zone to the rotational axis changes.

11. The method of claim 10, wherein the adjusting comprises adjusting the rate of translation along the radial path.

12. The method of claim 11, wherein for each position of the dispenser along the dispenser travel path, the dispenser and the center of the movable target zone are radially displaced from the rotational axis by a same distance.

* * * * *